US012727957B2

(12) United States Patent
Schorr et al.

(10) Patent No.: US 12,727,957 B2
(45) Date of Patent: Sep. 8, 2026

(54) CONTROL AND FEEDBACK BASED ON INSERTION FORCE

(71) Applicant: Intuitive Surgical Operations, Inc., Sunnyvale, CA (US)

(72) Inventors: Samuel B. Schorr, East Palo Alto, CA (US); Nicola Diolaiti, Menlo Park, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 633 days.

(21) Appl. No.: 17/784,021

(22) PCT Filed: Dec. 9, 2020

(86) PCT No.: PCT/US2020/064127
§ 371 (c)(1),
(2) Date: Jun. 9, 2022

(87) PCT Pub. No.: WO2021/119207
PCT Pub. Date: Jun. 17, 2021

(65) Prior Publication Data

US 2023/0017745 A1 Jan. 19, 2023

Related U.S. Application Data

(60) Provisional application No. 62/947,497, filed on Dec. 12, 2019.

(51) Int. Cl.
*A61B 34/00* (2016.01)
*A61B 34/20* (2016.01)
(Continued)

(52) U.S. Cl.
CPC .............. *A61B 34/76* (2016.02); *A61B 34/20* (2016.02); *A61B 34/37* (2016.02); *A61B 34/77* (2016.02);
(Continued)

(58) Field of Classification Search
CPC ......... A61B 34/76; A61B 34/20; A61B 34/37; A61B 34/77; A61B 90/06;
(Continued)

(56) References Cited

U.S. PATENT DOCUMENTS 8,945,095 B2 2/2015 Blumenkranz et al.
2007/0233044 A1 10/2007 Wallace et al.
(Continued)

FOREIGN PATENT DOCUMENTS

WO WO-2006091494 A1 * 8/2006 ......... A61B 17/1675
WO WO-2016154557 A1 * 9/2016 ............. A61B 34/10
(Continued)

OTHER PUBLICATIONS

Rajih E. et al.; Error reporting from the da Vinci surgical system in robotic surgery: a Canadian multispecialty experience at a single academic centre. Can Urol Assoc J. May 2017;11(5):E197-E202. doi: 10.5489/cuaj.4116. Epub May 9, 2017. PMID: 28503234; PMCID: PMC5426941. (Year: 2017).*
(Continued)

*Primary Examiner* — Jennifer Pitrak McDonald
*Assistant Examiner* — Christopher J Mutchler
(74) *Attorney, Agent, or Firm* — Schwegman, Lundberg & Woessner, P.A.

(57) ABSTRACT

A machine is configured to access force data generated by a force sensor, where the force sensor is communicatively coupled to a proximal portion of a flexible elongate device that has a distal portion configured to travel within an environment, and where the force sensor is configured to detect forces and generate the force data therefrom. The machine, based on the force data, identifies an insertion force encountered by the distal portion of the flexible elongate device from among the forces detected by the force sensor. The machine then, based on the identified insertion
(Continued)

force, initiates a responsive operation performed by a control system communicatively coupled to the flexible elongate device.

20 Claims, 13 Drawing Sheets

(51) Int. Cl.
*A61B 34/30* (2016.01)
*A61B 34/37* (2016.01)
*A61B 90/00* (2016.01)

(52) U.S. Cl.
CPC ...... *A61B 90/06* (2016.02); *A61B 2034/2061* (2016.02); *A61B 2034/301* (2016.02); *A61B 2090/064* (2016.02)

(58) Field of Classification Search
CPC ...... A61B 2034/2061; A61B 2034/301; A61B 2090/064; A61B 2017/00119; A61B 34/35; A61B 2034/303; A61B 2090/065; A61B 34/30
See application file for complete search history.

(56) References Cited

U.S. PATENT DOCUMENTS

| | | | | |
|---|---|---|---|---|
| 2007/0238987 | A1 | 10/2007 | Minai et al. | |
| 2008/0214372 | A1 | 9/2008 | Karp | |
| 2009/0275818 | A1 | 11/2009 | Rau et al. | |
| 2010/0121269 | A1 | 5/2010 | Goldenberg et al. | |
| 2011/0071543 | A1 * | 3/2011 | Prisco | A61B 34/76 600/118 |
| 2011/0295247 | A1 | 12/2011 | Schlesinger et al. | |
| 2011/0319910 | A1 | 12/2011 | Roelle et al. | |
| 2012/0165780 | A1 | 6/2012 | Bazargan et al. | |
| 2013/0002842 | A1 | 1/2013 | Das et al. | |
| 2015/0272684 | A1 * | 10/2015 | Tsusaka | A61B 34/37 700/253 |
| 2015/0359419 | A1 | 12/2015 | Hane et al. | |
| 2018/0177556 | A1 | 6/2018 | Noonan | |
| 2018/0231426 | A1 | 8/2018 | Hine | |
| 2018/0249919 | A1 | 9/2018 | Pont et al. | |
| 2018/0338806 | A1 | 11/2018 | Grubbs | |
| 2018/0338811 | A1 | 11/2018 | Miklos et al. | |
| 2019/0101876 | A1 | 4/2019 | Ghangam et al. | |

FOREIGN PATENT DOCUMENTS

| | | | |
|---|---|---|---|
| WO | WO-2018005842 | A1 | 1/2018 |
| WO | WO-2018005861 | A1 | 1/2018 |
| WO | WO-2018125917 | A1 | 7/2018 |
| WO | WO-2019074786 | A1 | 4/2019 |
| WO | WO-2019193952 | A1 | 10/2019 |
| WO | WO-2020055972 | A1 | 3/2020 |

OTHER PUBLICATIONS

J. Pile, G. B. Wanna and N. Simaan, "Force-based flexible path plans for robotic electrode insertion," 2014 IEEE International Conference on Robotics and Automation (ICRA), Hong Kong, China, 2014, pp. 297-303 (Year: 2014).*

International Preliminary Report on Patentability for Application No. PCT/US2019/050571, mailed on Mar. 25, 2021, 9 pages.

International Search Report and Written Opinion for Application No. PCT/US2019/050571, mailed on Dec. 16, 2019, 13 pages.

International Search Report and Written Opinion for Application No. PCT/US2020/064127, mailed on Mar. 17, 2021, 14 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Preliminary Report on Patentability for Application No. PCT/US2020/064127, mailed on Jun. 23, 2022, 10 pages.

* cited by examiner

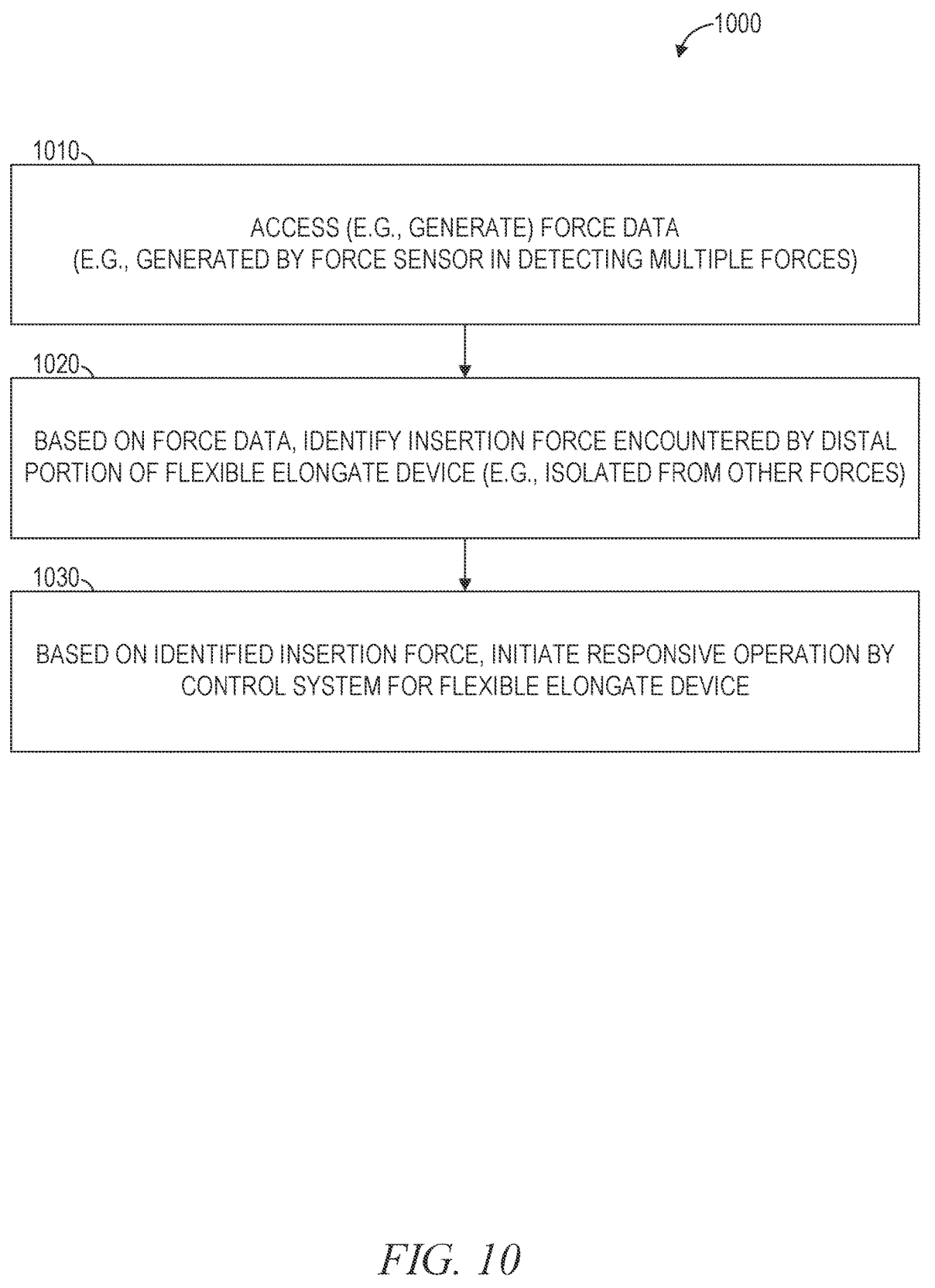

1000

1010

ACCESS (E.G., GENERATE) FORCE DATA
(E.G., GENERATED BY FORCE SENSOR IN DETECTING MULTIPLE FORCES)

1020

BASED ON FORCE DATA, IDENTIFY INSERTION FORCE ENCOUNTERED BY DISTAL PORTION OF FLEXIBLE ELONGATE DEVICE (E.G., ISOLATED FROM OTHER FORCES)

1030

BASED ON IDENTIFIED INSERTION FORCE, INITIATE RESPONSIVE OPERATION BY CONTROL SYSTEM FOR FLEXIBLE ELONGATE DEVICE

*FIG. 10*

CONTROL AND FEEDBACK BASED ON INSERTION FORCE

This application is a U.S. National Stage Filing under 35 U.S.C. 371 from International Application No. PCT/US2020/064127, filed on Dec. 9, 2020, and published as WO 2021/119207 A1 on Jun. 17, 2021, which claims the benefit of priority to U.S. Patent Application Ser. No. 62/947,497, filed on Dec. 12, 2019, each of which is incorporated by reference herein in its entirety.

TECHNICAL FIELD

The subject matter disclosed herein generally relates to the technical field of special-purpose machines that facilitate human control of a device (e.g., a robot or other device), including software-configured computerized variants of such special-purpose machines and improvements to such variants, and to the technologies by which such special-purpose machines become improved. Specifically, the present disclosure addresses systems and methods that, for example, in the process of facilitating human control of a device, facilitate device control or operator feedback based on a force encountered by the device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient's anatomy or through one or more surgical incisions. Through these natural orifices or incisions, surgeons or other clinicians may insert minimally invasive medical instruments (e.g., surgical, diagnostic, therapeutic, or biopsy instruments) to reach a target tissue location. One such minimally invasive technique is to use a flexible, steerable elongate device (e.g., a catheter) that can be inserted into anatomic passageways and navigated toward a region of interest within the patient's anatomy. Control of such an elongate device by medical personnel during an image-guided procedure involves the management of several degrees of freedom, which may include managing insertion or retraction of the elongate device, steering the device, managing the bend radius of the device, or any suitable combination thereof.

Accordingly, it would be beneficial to provide a control system that supports intuitive control and management of medical instruments, including elongate devices, such as flexible and steerable catheters, that are suitable for performing minimally invasive medical techniques.

SUMMARY

Example embodiments discussed herein are best summarized by the claims that follow the description.

In some example embodiments, a system includes:

a flexible elongate device including a distal portion configured to travel within an environment and a proximal portion configured to remain external to the environment;

a force sensor coupled to the proximal portion of the flexible elongate device and configured to detect forces and generate force data based on the detected forces; and a control system communicatively coupled to the flexible elongate device and the force sensor, the control system being configured to:

based on the force data, identify an insertion force encountered by the distal portion of the flexible elongate device from among the forces detected by the force sensor; and based on the identified insertion force encountered by the distal portion, initiate a responsive operation performed by the control system.

In various example embodiments, a machine-readable medium includes instructions that, when executed by one or more processors of a machine, cause the machine to perform operations including:

accessing force data generated by a force sensor communicatively coupled to a proximal portion of a flexible elongate device that has a distal portion configured to travel within an environment, the force sensor being configured to detect forces and generate the force data therefrom:

based on the force data, identifying an insertion force encountered by the distal portion of the flexible elongate device from among the forces detected by the force sensor; and based on the identified insertion force, initiating a responsive operation performed by a control system communicatively coupled to the flexible elongate device.

In certain example embodiments, a method includes:

accessing, by one or more processors, force data generated by a force sensor communicatively coupled to a proximal portion of a flexible elongate device that has a distal portion configured to travel within an environment, the force sensor being configured to detect forces and generate the force data therefrom;

based on the force data, and by one or more of the processors, identifying an insertion force encountered by the distal portion of the flexible elongate device from among the forces detected by the force sensor; and based on the identified insertion force, and by one or more of the processors, initiating a responsive operation performed by a control system communicatively coupled to the flexible elongate device.

In some example embodiments, a system includes: an elongate device including a distal portion configured to travel within an environment; a force sensor coupled to the elongate device and configured to measure a force encountered by the distal portion of the elongate device during a time period in which the distal portion travels a distance within the environment, the force sensor being configured to generate force data based on the measured force; a display screen; one or more processors; and a memory storing instructions that, when executed by at least one processor among the one or more processors, cause the at least one processor to perform operations including: accessing the force data generated by the force sensor, the force data quantifying variation in magnitude of the force encountered by the distal portion of the elongate device during the time period in which the distal portion traveled the distance within the environment, the force data including a current value of the magnitude of the force; determining a temporal rate of change of the force during the time period based on the force data and the time period; determining a spatial rate of change of the force based on the force data and the distance traveled by the distal portion of the elongate device; generating a graphical representation of the force based on the current value of the magnitude of the force, the temporal rate of change of the force, and the spatial rate of change of the force; and causing the display screen to present the graphical representation generated based on the current value, the temporal rate of change, and the spatial rate of change.

In certain example embodiments, a method includes: accessing force data generated by a force sensor, the force data quantifying variation in magnitude of a force encountered by a distal portion of an elongate device during a time period in which the distal portion traveled a distance within an environment, the force data including a current value of the magnitude of the force; determining a temporal rate of change of the force during the time period based on the force data and the time period; determining a spatial rate of change of the force based on the force data and the distance traveled by the distal portion of the elongate device; generating a graphical representation of the force based on the current value of the magnitude of the force, the temporal rate of change of the force, and the spatial rate of change of the force; and causing the display screen to present the graphical representation generated based on the current value, the temporal rate of change, and the spatial rate of change.

In various example embodiments, a machine-readable medium includes instructions that, when executed by one or more processors of a machine, cause the machine to perform operations including: accessing force data generated by a force sensor, the force data quantifying variation in magnitude of a force encountered by a distal portion of an elongate device during a time period in which the distal portion traveled a distance within an environment, the force data including a current value of the magnitude of the force; determining a temporal rate of change of the force during the time period based on the force data and the time period; determining a spatial rate of change of the force based on the force data and the distance traveled by the distal portion of the elongate device; generating a graphical representation of the force based on the current value of the magnitude of the force, the temporal rate of change of the force, and the spatial rate of change of the force; and causing the display screen to present the graphical representation generated based on the current value, the temporal rate of change, and the spatial rate of change.

BRIEF DESCRIPTION OF THE DRAWINGS

Some embodiments are illustrated by way of example and not limitation in the figures of the accompanying drawings.

FIGS. 10-12 are flowcharts illustrating operations of the control system in performing a method of providing feedback about the elongate device, control of the elongate device, or both, based on insertion force, according to some example embodiments.

DETAILED DESCRIPTION

Figure 1:
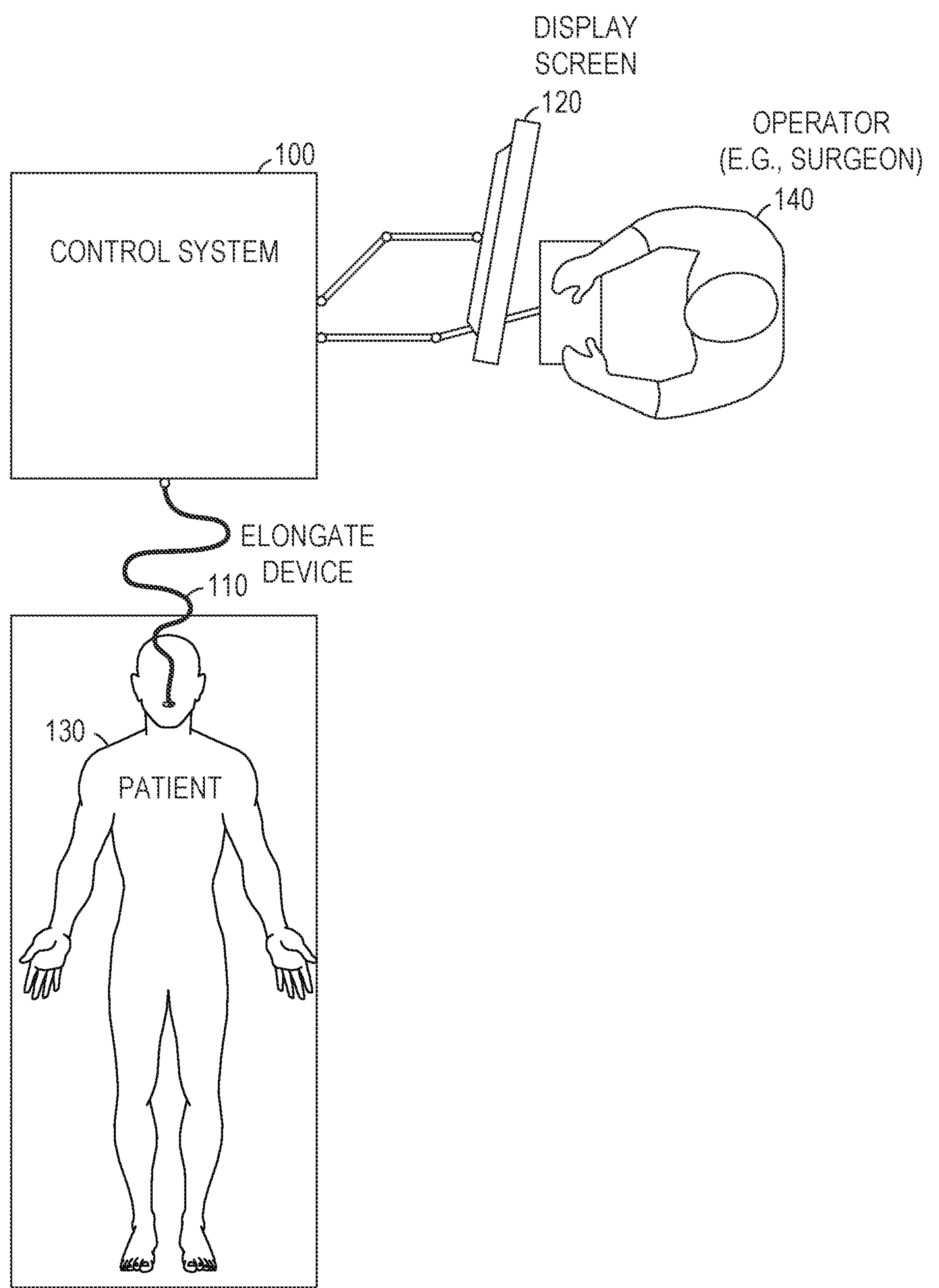
FIG. 1 is a diagram illustrating an elongate device being controlled by a control system and its operator (e.g., a surgeon), according to some example embodiments.

Example methods (e.g., algorithms) facilitate generating a graphical representation of force (e.g., for presentation in a graphical user interface (GUI)), and example systems (e.g., special-purpose machines configured by special-purpose software) are configured to facilitate generating a graphical representation of force. Examples merely typify possible variations. Unless explicitly stated otherwise, structures (e.g., structural components, such as modules) are optional and may be combined or subdivided, and operations (e.g., in a procedure, algorithm, or other function) may vary in sequence or be combined or subdivided. In the following description, for purposes of explanation, numerous specific details are set forth to provide a thorough understanding of various example embodiments. It will be evident to one skilled in the art, however, that the present subject matter may be practiced without these specific details.

A machine may form all or part of a control system that is configured (e.g., by suitable hardware, software, or both) to interact with one or more users by identifying a force (e.g., estimating an insertion force) encountered by a device or a portion thereof (e.g., a distal portion of an elongate device) and providing operator feedback based on the identified force, providing enhanced control of the device based on the identified force, or both. In the example context of a surgeon performing robotic surgery, the machine may be configured to access force data (e.g., via generation, retrieval, or receipt of the force data) generated by a force sensor communicatively coupled to a proximal portion of a flexible elongate device, where the flexible elongate device has a distal portion configured to travel within an environment, and where the force sensor is configured to detect forces and generate the force data therefrom. Based on the accessed force data, the machine identifies an insertion force encountered by a distal portion of the flexible elongate device from among the forces detected by the force sensor.

Based on the identified insertion force, the machine initiates a responsive operation to be performed by the control system for the flexible elongate device, with the control system being communicatively coupled to the flexible elongate device. Examples of such a responsive operation include providing haptic (e.g., vibrational) force feedback to the surgeon, scaling how user input (e.g., by the surgeon) is mapped to controlling movements of the distal portion (e.g., a catheter tip) of the elongate device, providing an alert regarding the insertion force (e.g., audible beeps, tones, or recorded or synthesized speech warnings or other messages), providing a recommendation to alter a workflow in performing the robotic surgery (e.g., to re-lubricate the elongate device, to alter its configuration, to withdraw the elongate device and seek service, etc.), resisting one or more user inputs (e.g., resisting forward motion of a controller device that would drive the distal portion of the elongate device forward), preventing results of one or more user inputs (e.g., blocking, ignoring, or disabling forward motion of the controller device that otherwise would drive the distal portion of the elongate device forward), or any suitable combination thereof.

A machine may form all or part of a control system that is configured (e.g., by suitable hardware, software, or both)

to interact with one or more users by generating and providing graphical representations of various data (e.g., in real time), including generating and providing a graphical representation of a force. In the example context of a surgeon performing robotic surgery, the machine may be configured to access force data generated by a force sensor, where the force data quantifies variation in magnitude of a force encountered by a distal portion of an elongate device (e.g., a robotic surgical catheter inserted into a human patient) during a time period in which the distal portion traveled a distance within an environment (e.g., the human patient), and where the force data includes a current value of the magnitude of the force. The machine may then determine (e.g., by calculation) two rates of change of the force, namely, a temporal rate of change of the force during the time period and a spatial rate of change of the force over the distance traveled. The temporal rate of change may be determined based on the force data and the time period, and the spatial rate of change may be determined based on the force data and the distance traveled by the distal portion of the elongate device. The machine then generates a graphical representation of the force based on the current value of the magnitude of the force, the temporal rate of change of the force, and the spatial rate of change of the force. The machine may accordingly cause a display screen to present the graphical representation to a user (e.g., the surgeon).

FIG. 1 is a diagram illustrating an elongate device 110 being controlled (e.g., navigated, moved, inserted, withdrawn, or otherwise manipulated) by a control system 100 and its operator 140 (e.g., a surgeon, clinician, or physician), according to some example embodiments. The control system 100 may be or include a teleoperated medical system that is configured or otherwise suitable for use in medical procedures, such as surgical, diagnostic, therapeutic, or biopsy procedures. As shown in FIG. 1, the control system 100 includes and controls (e.g., guides) the elongate device 110, which may form all or part of a medical instrument suitable for performing various medical procedures on a patient 130. In some example embodiments, the proximal portion (e.g., the proximal end or proximate end) of the elongate device 110 is mounted on or near an operating table upon which the patient 130 is lying, while the distal portion (e.g., the distal end) of the elongate device 110 is inserted into the anatomy of the patient 130 (e.g., through an incision therein or an orifice thereof).

The operator 140 may be located at a physician's console, which may be located in the same room as the patient 130, such as at the side of a surgical table on which patient 130 located. However, the operator 140 may be located in a different room or a completely different building from the patient 130. The control system 100 may include one or more control devices for controlling the elongate device 110 (e.g., by actuating one or more actuators within the elongate device 110). Such control devices may be or include various input devices, such as joysticks, trackballs, data gloves, trigger-guns, hand-operated controllers, voice recognition devices, body motion or presence sensors, or any suitable combination thereof. To provide the operator 140 with a strong sense of directly controlling the elongate device 110, such control devices may be configured to operate with the same degrees of freedom as the elongate device 110. In this manner, the control devices provide operator 140 with telepresence or the perception that the control devices are integral with the elongate device 110.

In some example embodiments, the control devices may have more or fewer degrees of freedom than the elongate device 110 and still provide the operator 140 with the above-described telepresence. According to certain embodiments, the control devices may optionally be manual input devices which move with six degrees of freedom, and which may also include an actuation handle for actuating one or more instruments at the distal portion of the elongate device 110 (e.g., for closing grasping jaws, applying an electrical potential to an electrode, delivering a medicinal treatment, or any suitable combination thereof).

The control system 100 additionally controls a display screen 120, which may be configured to display an image or other representation of the surgical site and the elongate device 110. Such an image may be generated by the control system 100. The display screen 120 may be oriented so that the operator 140 can control the elongate device 110 with the perception of telepresence.

In certain example embodiments, the elongate device 110 may include a visualization system, such as a viewing scope assembly that records a current (e.g., real-time) image of a surgical site and provides the image to the operator 140 through one or more displays, such as the display screen 120. For example, the current image may be a two-dimensional or three-dimensional image captured by an endoscope positioned (e.g., by the distal portion of the elongate device 110) within the surgical site. According to some embodiments, the visualization system includes endoscopic components that may be integrally or removably coupled to elongate device 110. However, in some embodiments, a separate endoscope, attached to a separate manipulation device, may be used with the elongate device 110 to image the surgical site. The visualization system may be implemented as hardware, firmware, software, or any suitable combination thereof, which interact with or are otherwise executed by one or more computer processors, which may include one or more processors of the control system 100.

The display screen 120 may display an image of the surgical site and medical instruments captured by the visualization system. In addition, the display screen 120 may present one or more images of a surgical site recorded pre-operatively or intra-operatively using image data from imaging technology such as computed tomography (CT), magnetic resonance imaging (MRI), fluoroscopy, thermography, ultrasound, optical coherence tomography (OCT), thermal imaging, impedance imaging, laser imaging, nanotube X-ray imaging, or any suitable combination thereof. The pre-operative or intra-operative image data may be presented as two-dimensional, three-dimensional, or four-dimensional (e.g., showing time-based or velocity-based information) images, as images that depict one or more models of the patient 130 or a portion of the anatomy thereof, or both.

The display screen 120 may display a navigational image in which the actual location of the elongate device 110 (e.g., the distal portion thereof) is shown with pre-operative or current images. This may be done to present the operator 140 with a navigational image of the internal surgical site from the viewpoint of the elongate device 110 (e.g., the distal portion thereof). In some example embodiments, the viewpoint may be the view looking forward from a tip of the elongate device 110 (e.g., the distal end thereof). An image of the tip of the elongate device 110 (e.g., along with one or more other graphical or alphanumeric indicators) may be superimposed on the navigational image to assist the operator 140 in controlling the elongate device 110. In certain example embodiments, the elongate device 110 is not visible in the navigational image. In certain example embodiments, the viewpoint may be the view looking towards the patient 130 from an external location. An image of all or a portion of the elongate device 110 (e.g., along with one or more other graphical or alphanumeric indicators) may be superimposed on the navigational image to assist the operator 140 in controlling the elongate device 110.

The elongate device 110 may extend into an internal surgical site within the anatomy (e.g., the body) of the patient 130 via an opening (e.g., an incision or in orifice) in the anatomy of the patient 130. The control system 100 may receive feedback from the elongate device 110 (e.g., force, torque, shape, position, velocity, or any suitable combination thereof). Responsive to the feedback, the control system 100 may cause the display screen 120 to present one or more graphical representations of the feedback within a GUI.

Figure 2:
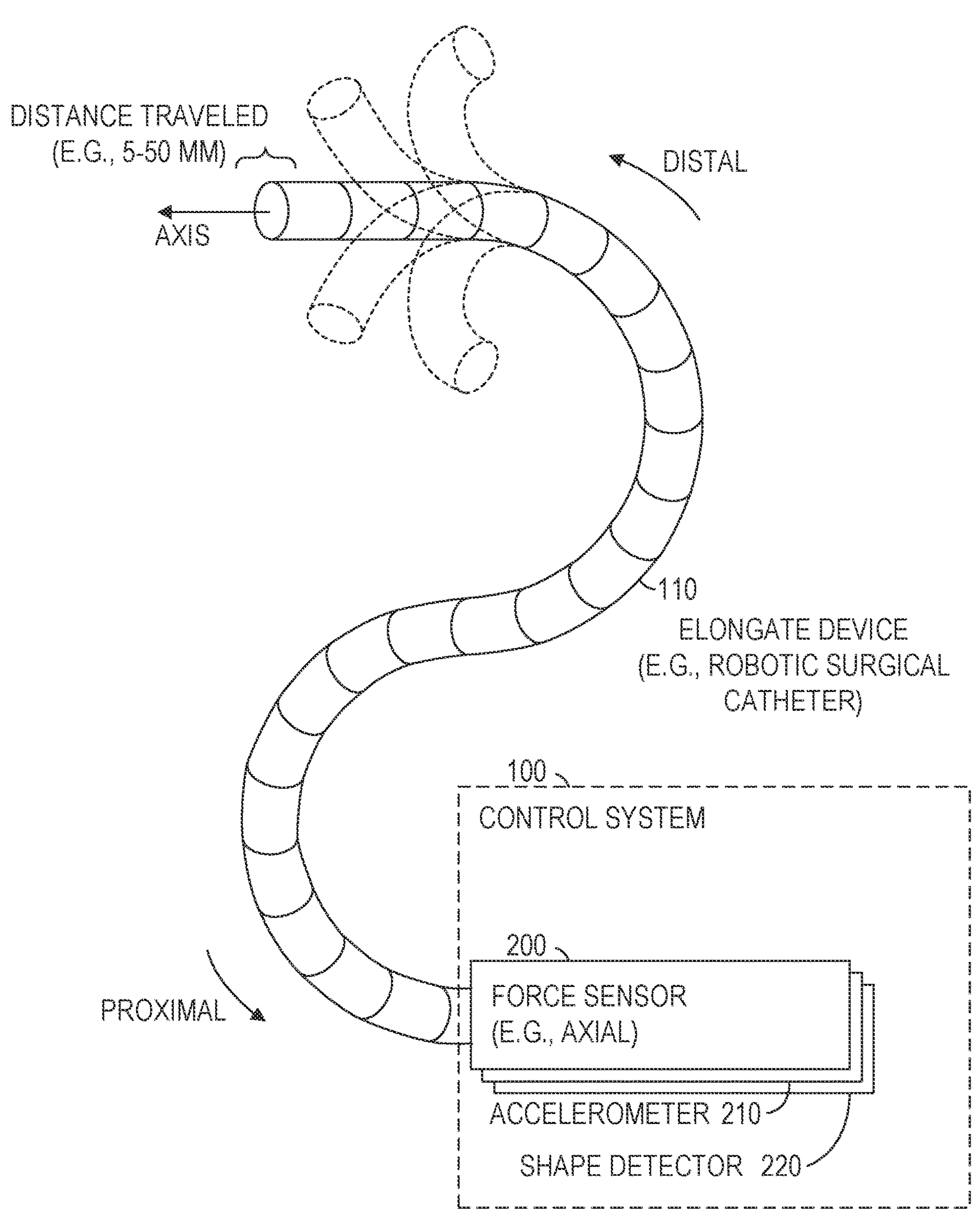
FIG. 2 is a diagram illustrating the elongate device and its control system, according to some example embodiments.

FIG. 2 is a diagram illustrating the elongate device 110 and its control system 100, according to some example embodiments. The elongate device 110 is illustrated in the example form of a robotic surgical catheter and includes a flexible body that has a proximal portion (e.g., terminating in a proximal end) and a distal portion (e.g., terminating in a distal end or distal tip). Accordingly, the elongate device 110 may have an axis that runs the length of the elongate device 110 in an axial direction from the proximal portion to the distal portion. In some example embodiments, the elongate device 110 has an outer diameter of approximately 3 millimeters, though other outer diameters are contemplated. In some example embodiments, the elongate device 110 includes multiple body segments which may be individually or collectively actuated to provide flexibility in movement.

As shown in FIG. 2, the distal portion (e.g., the distal tip) of the elongate device 110 can be controllably navigated within an environment (e.g., within the anatomy of the patient 130), such that the distal portion travels an incremental distance (e.g., 5-50 millimeters) through the environment. FIG. 2 further depicts the control system 100 as including a force sensor 200 (e.g., an axial force sensor), an accelerometer 210, and a shape detector 220. The force sensor 200 may be coupled (e.g., mechanically, communicatively, or both) to the elongate device 110 and configured to detect (e.g., measure) a force encountered by at least the distal portion of the elongate device 110 (e.g., with or without gravitational and frictional forces acting on the entirety of the elongate device 110). The accelerometer 210 may be coupled to the elongate device 110 and configured to detect (e.g., measure) acceleration (e.g., due to gravity, friction, or both) encountered by the elongate device 110 or a portion thereof. The shape detector 220 may be coupled to the elongate device 110 and configured to detect a shape of the elongate device 110 (e.g., detecting positions, orientations, or both of multiple segments of the elongate device 110). One or both of the accelerometer 210 and the shape detector 220 may be located in any suitable location within or coupled to the elongate device 110, including the example locations shown in FIG. 2.

Figure 3:
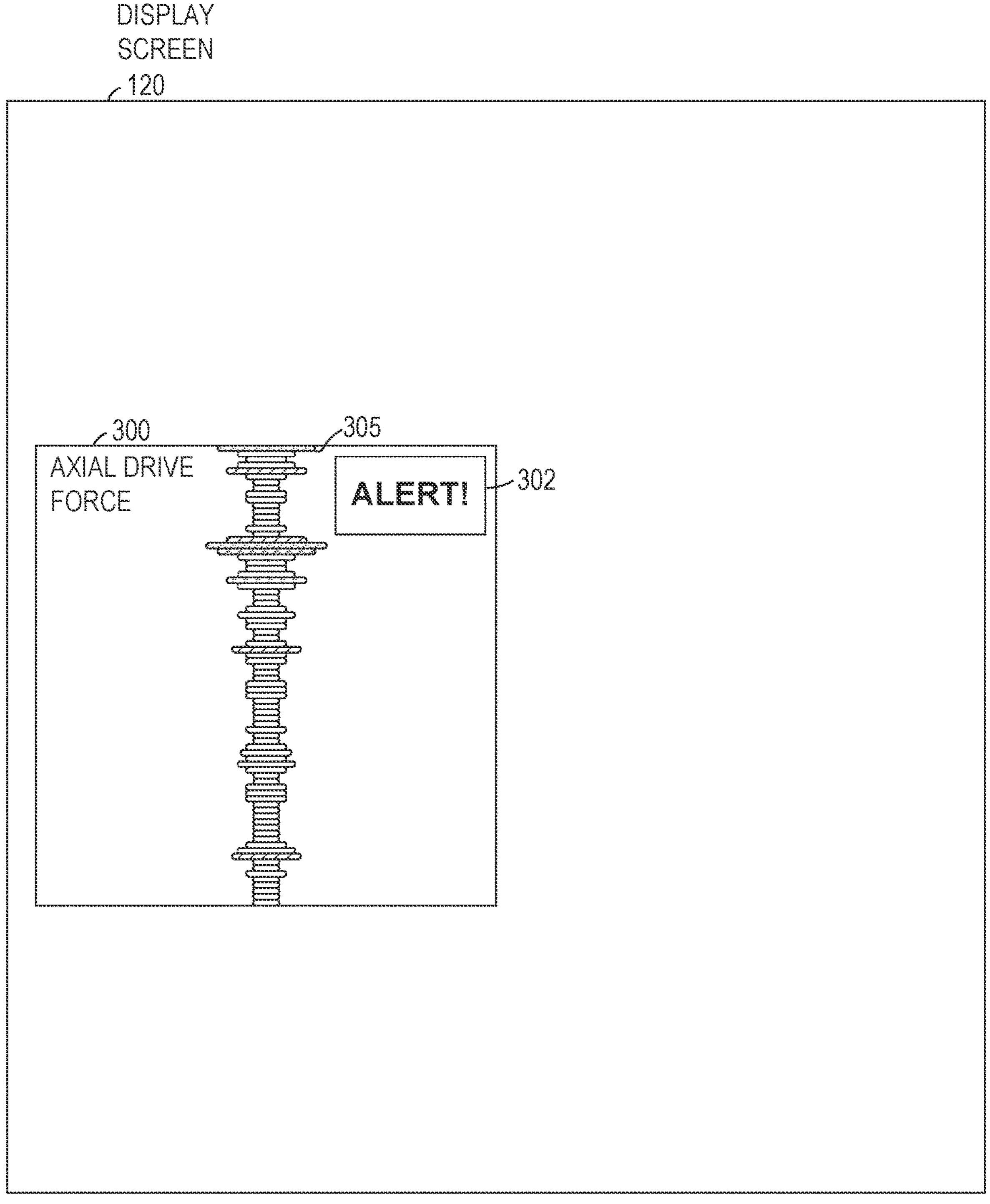
FIGS. 3 and 4 are screenshots of a portion of a display screen that is presenting a graphical representation of force, according to some example embodiments.
Figure 4:
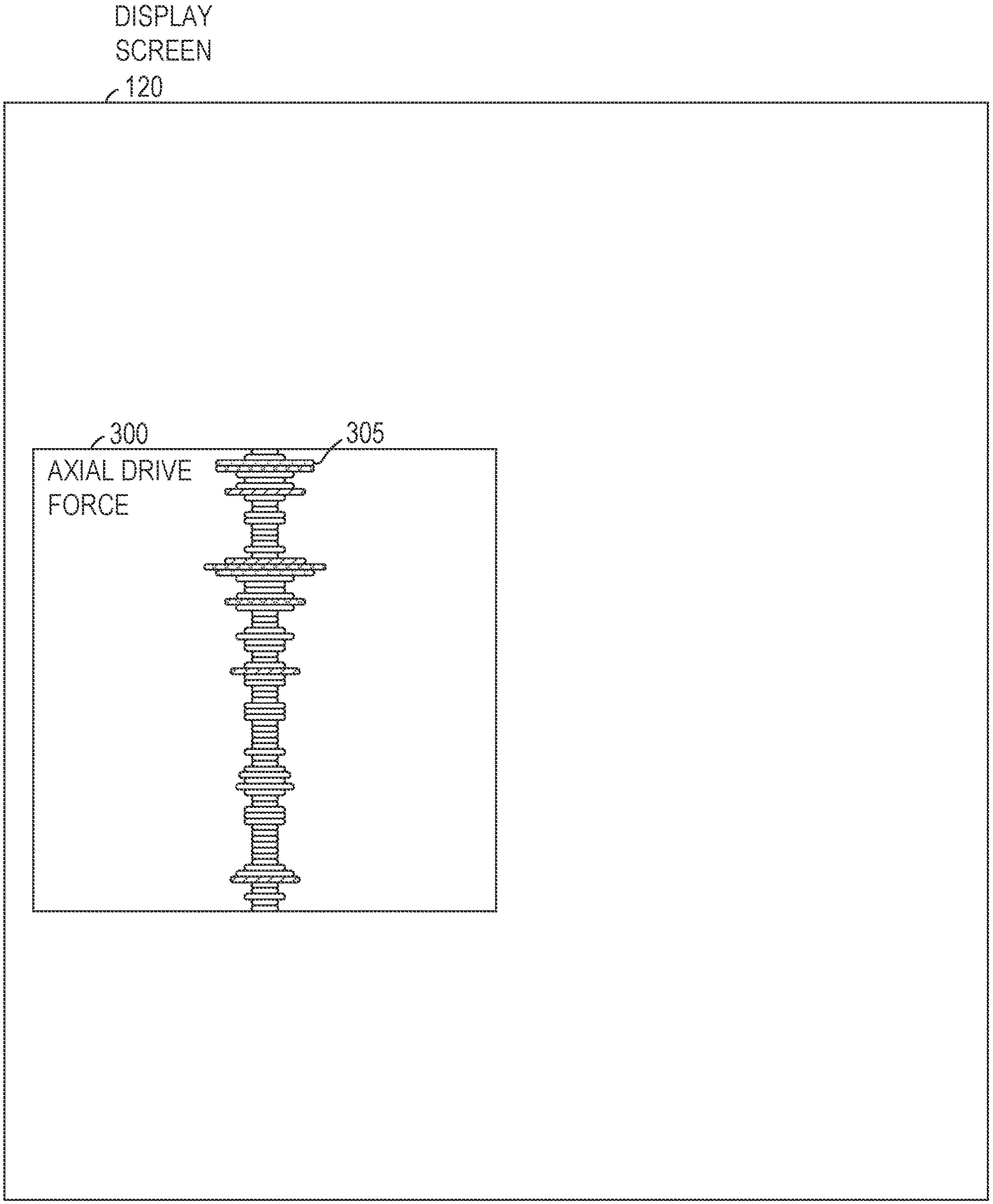

FIGS. 3 and 4 are screenshots of a portion of the display screen 120 that is presenting a graphical representation 300 of force, according to some example embodiments. As shown in FIGS. 3 and 4, the graphical representation 300 takes the example form of a window that forms all or part of a GUI presented by the display screen 120. Such a GUI may provide the operator 140 with some or all of the visual feedback generated by the control system 100 (e.g., in controlling the elongate device 110 through the process of performing a medical procedure on the patient 130). Accordingly, in the example embodiments illustrated in FIGS. 3 and 4, the graphical representation 300 may present the operator 140 with visual feedback that is indicative or otherwise based on a force encountered by the elongate device 110 or a portion thereof (e.g., an axial force encountered by the distal portion of the elongate device 110).

As shown in FIG. 3, at a particular point in time, the graphical representation 300 may present current information about the current value of the magnitude of the force encountered by the elongate device 110, as well as historical information about historical values of the magnitude of the force. For example, the graphical representation 300 may show live information in real-time, as well as a sliding portion of the most recent historical information (e.g., within the past 5-30 seconds). In FIG. 3, the graphical representation 300 includes a bar 305, which as illustrated is the most current (e.g., latest) bar within a sequence of bars that each represent the magnitude of the force during a corresponding period of time (e.g., an incremental period of time in which the distal portion of the elongate device 110 traveled an incremental distance). The bar 305 may form all or part of a portion of the graphical representation 300, and this portion may be colored (e.g., highlighted with a contrasting or other attention-attracting color) based on the current value of the magnitude of the force, the temporal rate of change of the force, the spatial rate of change of the force, or any suitable combination thereof.

Furthermore, although the bar 305 is shown in FIG. 3 as a symmetric indicator of the current value of the magnitude of the force, certain example embodiments utilize an asymmetrical variant of the bar 305. For example, the bar 305 may extend to the right of a marked or unmarked axis to indicate one direction (e.g., insertion) of the force, and the bar 305 may extend to the left of the axis to indicate another direction (e.g., retraction or otherwise opposing) of the force.

According to various example embodiments, the sequence of bars is slowly moving in one axis (e.g., vertically downward) within the graphical representation 300, and the size of each bar (e.g., bar 305) is linearly or nonlinearly representative of the current value of the magnitude of the force during the corresponding period of time. For example, the cross-axis (e.g., horizontal) length of the bar 305 may be linearly proportional to the current value of the magnitude of the force, based on the current value falling within a predetermined range of values (e.g., above a minimum threshold value, below a maximum threshold value, or both), and the cross-axis length of the bar 305 may be nonlinearly representative (e.g., upscaled or downscaled) of the current value of the magnitude of the force, based on the current value falling outside such a predetermined range of values. In some example embodiments, the axis-aligned (e.g., vertical) length of each bar (e.g., bar 305) is linearly or nonlinearly representative of the duration of the corresponding period of time.

Moreover, in some example embodiments, the cross-axis length of each bar (e.g., bar 305) may be individually adjusted (e.g., when being rendered for addition to the sequence of bars). For example, instead of being scaled based on one or more threshold values, the cross-axis length of a bar (e.g., bar 305) may be determined based on a non-linear scaling function (e.g., $f(x)=x^3$, which attenuates the output when the input is less than unity and amplifies the output when the input exceeds unity).

In addition, FIG. 3 illustrates the graphical representation 300 as including an alert notification 302 (e.g., "ALERT!" or "TISSUE WALL PUNCTURE DANGER!"), which may be presented in response to detection of one or more predetermined conditions. As will be discussed in greater detail below, the control system 100 may detect such conditions based on the current value of the magnitude of the force, the temporal rate of change of the force, the spatial rate of change of the force, or any suitable combination thereof, as well as one or more additional factors (e.g., acceleration data, shape data, or both). Based on such factors, the control system 100 may infer that the distal portion of the elongate device 110 is encountering a blockage, excessive environmental friction, normal environmental friction, or abnormally low environmental friction. Accordingly, presentation of the alert notification may assist the operator 140 in understanding whether the distal portion of the elongate device 110 is being navigated as expected through the environment (e.g., through the anatomy of the patient 130).

As shown in FIG. 4, at a later point in time, the graphical representation 300 may continue to present further current information about the current value of the magnitude of the force encountered by the elongate device 110, as well as historical information about historical values of the magnitude of the force. In the example shown, the graphical representation 300 continues to show live information real-time, as well as the sliding portion of the most recent historical information. Accordingly, the bar 305 is no longer the most current bar within the sequence of bars in the graphical representation 300, though its color may continue to be determined based on the same factors as before (e.g., the then-current value of the magnitude of the force, the then-current temporal rate of change of the force, the then-current spatial rate of change of the force, or any suitable combination thereof). In FIG. 4, the graphical representation 300 no longer shows the alert notification 302. This may be in response to detecting the absence of the one or more predetermined conditions that triggered the presentation of the alert notification shown in FIG. 3.

Figure 5:
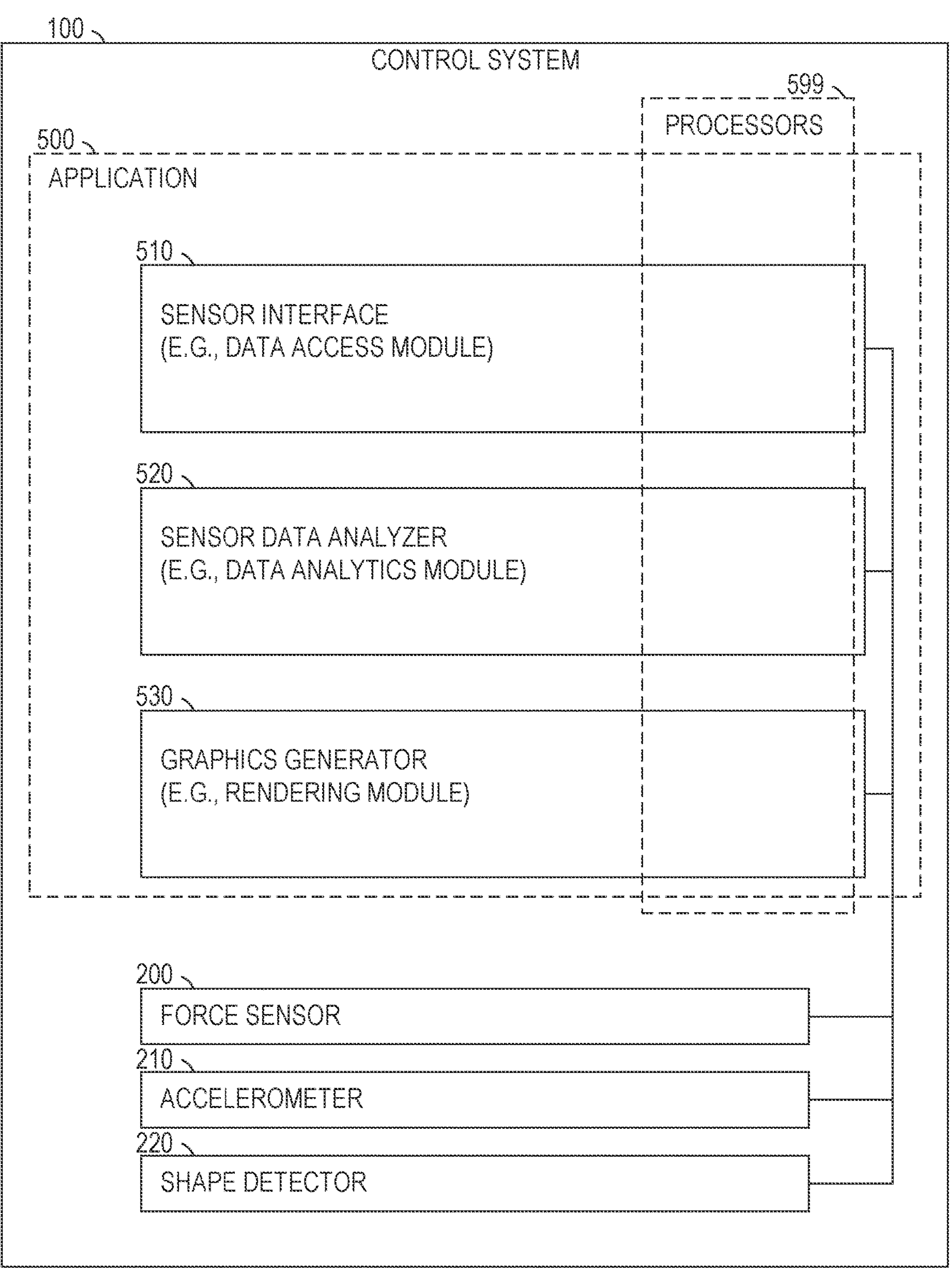
FIG. 5 is a block diagram illustrating components of the control system for the elongate device, according to some example embodiments.

FIG. 5 is a block diagram illustrating components of the control system 100 for the elongate device 110 (e.g., as described above with respect to FIGS. 1 and 2), according to some example embodiments. The control system 100 is shown in the example form of a machine (e.g., a machine that is or includes a computer system) that includes a sensor interface 510, a sensor data analyzer 520, and a graphics generator 530, all configured to communicate with each other (e.g., via a bus, shared memory, or a switch). Additionally, the control system 100 is shown in FIG. 5 as including the force sensor 200, the accelerometer 210, and the shape detector 220, which were introduced above.

The sensor interface 510 may be or include a data access module or similarly suitable code configured to access data from one or more sensors (e.g., the force sensor 200, the accelerometer 210, the shape detector 220, or any suitable combination thereof). The sensor data analyzer 520 may be or include a data analytics module or similarly suitable code configured to analyze the data accessed by the sensor interface 510. The graphics generator 530 may be or include a rendering module (e.g., a GUI rendering module) or similarly suitable code configured to render or otherwise generate graphics, such as the graphical representation 300, which was introduced above.

As shown in FIG. 5, the sensor interface 510, the sensor data analyzer 520, the graphics generator 530, or any suitable combination thereof may form all or part of an application 500 (e.g., a server application, a client application, a mobile app, or any suitable combination thereof) that is stored (e.g., installed) on the control system 100 for execution thereon. Furthermore, one or more processors 599 (e.g., hardware processors, digital processors, or any suitable combination thereof) may be included (e.g., temporarily or permanently) in the application 500, the sensor interface 510, the sensor data analyzer 520, the graphics generator 530, or any suitable combination thereof.

Any one or more of the components (e.g., modules) described herein may be implemented using hardware alone (e.g., one or more of the processors 599) or a combination of hardware and software. For example, any component described herein may physically include an arrangement of one or more of the processors 599 (e.g., a subset of or among the processors 599) configured to perform the operations described herein for that component. As another example, any component described herein may include software, hardware, or both, that configure an arrangement of one or more of the processors 599 to perform the operations described herein for that component. Accordingly, different components described herein may include and configure different arrangements of the processors 599 at different points in time or a single arrangement of the processors 599 at different points in time. Each component (e.g., module) described herein is an example of a means for performing the operations described herein for that component. Moreover, any two or more components described herein may be combined into a single component, and the functions described herein for a single component may be subdivided among multiple components. Furthermore, according to various example embodiments, components described herein as being implemented within a single system or machine (e.g., a single device) may be distributed across multiple systems or machines (e.g., multiple devices).

Any of the systems or machines (e.g., devices) discussed herein may be, include, or otherwise be implemented in a special-purpose (e.g., specialized or otherwise non-conventional and non-generic) computer that has been modified to perform one or more of the functions described herein for that system or machine (e.g., configured or programmed by special-purpose software, such as one or more software modules of a special-purpose application, operating system, firmware, middleware, or other software program). For example, a special-purpose computer system able to implement any one or more of the methodologies described herein is discussed below with respect to FIG. 13, and such a special-purpose computer may accordingly be a means for performing any one or more of the methodologies discussed herein. Within the technical field of such special-purpose computers, a special-purpose computer that has been specially modified (e.g., configured by special-purpose software) by the structures discussed herein to perform the functions discussed herein is technically improved compared to other special-purpose computers that lack the structures discussed herein or are otherwise unable to perform the functions discussed herein. Accordingly, a special-purpose machine configured according to the systems and methods discussed herein provides an improvement to the technology of similar special-purpose machines. Moreover, any two or more of the systems or machines discussed herein may be combined into a single system or machine, and the functions described herein for any single system or machine may be subdivided among multiple systems or machines.

Figure 6:
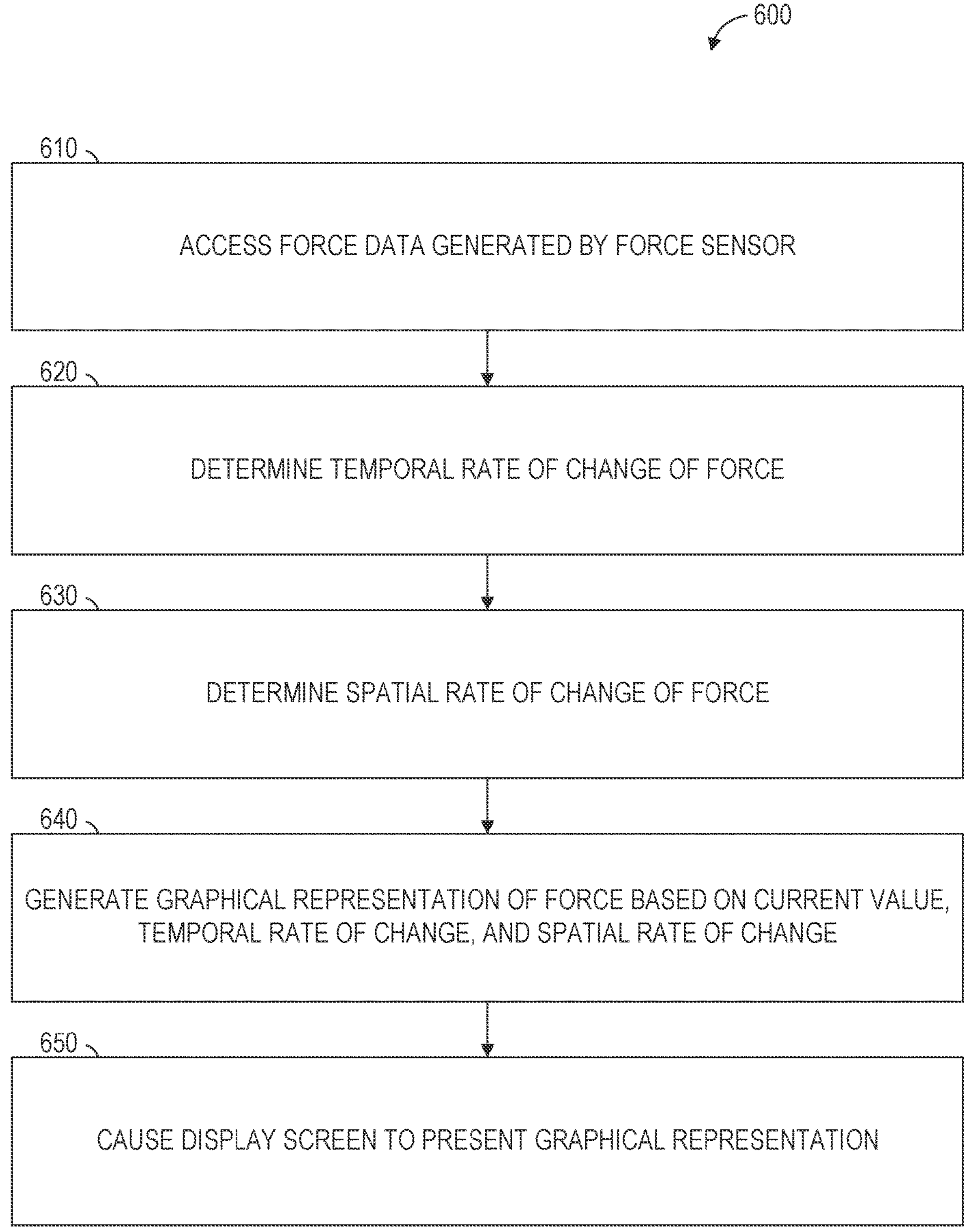
FIGS. 6-9 are flowcharts illustrating operations of the control system in performing a method of generating a graphical representation of force, according to some example embodiments.

FIGS. 6-9 are flowcharts illustrating operations of the control system 100 (e.g., as described above with respect to FIG. 5, in the context described above with respect to FIGS. 1 and 2, or both) in performing a method 600 of generating the graphical representation 300 of force, according to some example embodiments. Operations in the method 600 may be performed using components (e.g., modules) described above with respect to FIG. 5, using one or more processors (e.g., microprocessors or other hardware processors), or using any suitable combination thereof. As shown in FIG. 6, the method 600 includes operations 610, 620, 630, 640, and 650.

In operation 610, the sensor interface 510 accesses force data generated by the force sensor 200. The force data quantifies variation in magnitude of a force encountered by the distal portion of the elongate device 110. Specifically, the force sensor 200 is configured to measure the force encountered by the distal portion of the elongate device 110, and the force may be encountered and measured during a time period in which the distal portion of the elongate device 110 travels an incremental distance within an environment, such as within the anatomy of the patient 130. The force sensor 200 is further configured to generate the force data based on the measured force. The generated force data accessed in operation 610 may be live (e.g., real-time) force data and accordingly may include a current value of the magnitude of the force.

In operation 620, the sensor data analyzer 520 determines a temporal rate of change of the force during the time period in which the distal portion of the elongate device 110 traveled the incremental distance within the environment. This may be performed by calculating the temporal rate of change of the force based on the force data accessed in operation 610 and the duration of the time period in which the distal portion of the elongate device 110 traveled the incremental distance.

In operation 630, the sensor data analyzer 520 determines a spatial rate of change of the force over the incremental distance traveled by the distal portion of the elongate device 110. This may be performed by calculating the spatial rate of change of the force based on the force data accessed in operation 610 and the traveled incremental distance.

In operation 640, the graphics generator 530 generates the graphical representation 300 of the force encountered by the distal portion of the elongate device 110. This may be performed by generating the graphical representation 300 (e.g., as all or part of a GUI to be presented by the display screen 120) based on the current value of the magnitude of the force, the temporal rate of change of the force (e.g., as calculated in operation 620), the spatial rate of change of the force (e.g., as calculated in operation 630), or any suitable combination thereof.

In operation 650, the graphics generator 530 causes the display screen 120 to present the graphical representation 300 that was generated in operation 640. This may be performed by providing the generated graphical representation 300 to the display screen 120 (e.g., within a GUI, within a video signal, or both). Accordingly, performance of operation 650 may have the effect of communicating the graphical representation 300 (e.g., with or without an alert notification) to the operator 140 of the control system 100.

Figure 7:
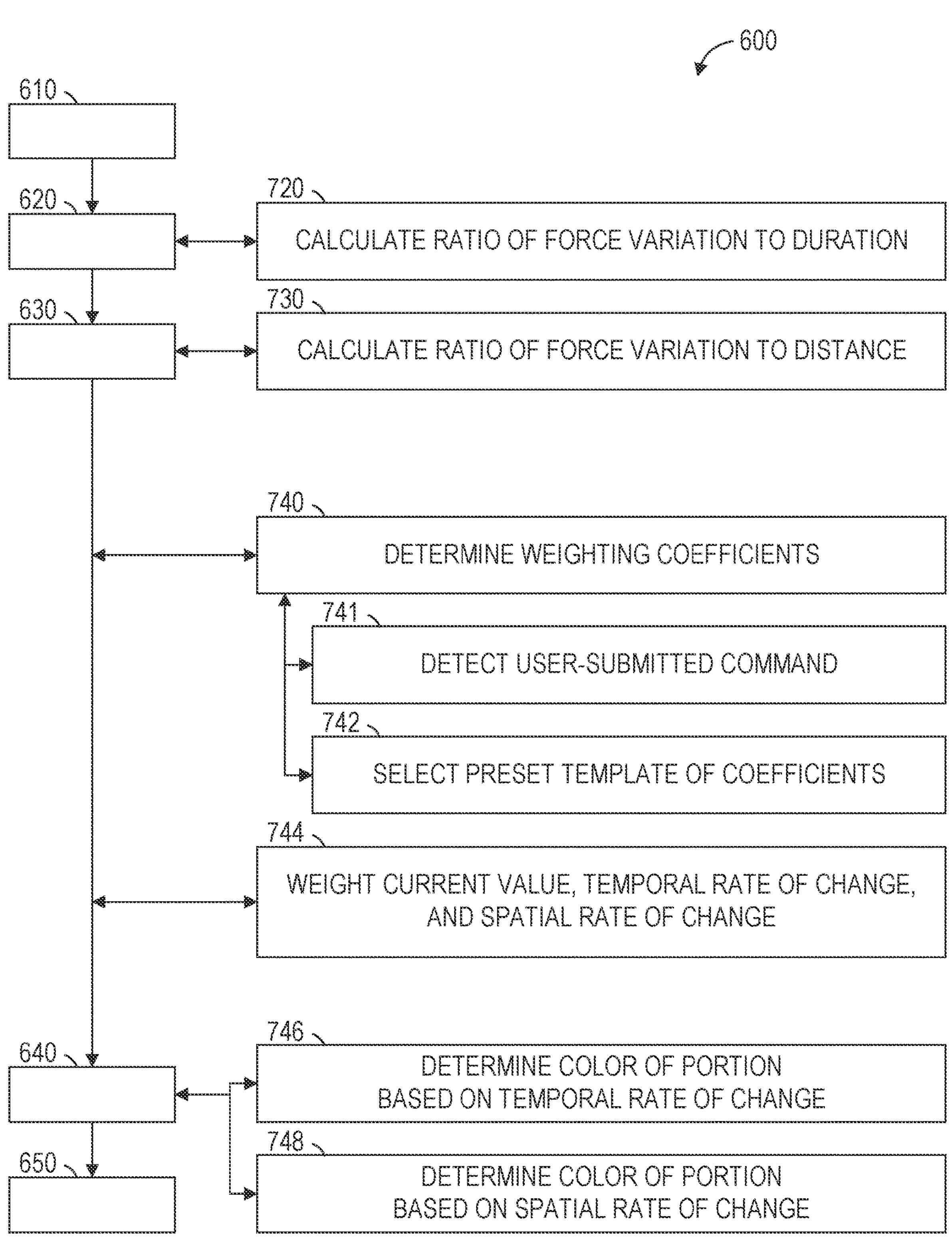

As shown in FIG. 7, in addition to any one or more of the operations previously described, the method 600 may include one or more of operations 720, 730, 740, 741, 742, 744, 746, and 748.

Operation 720 may be performed as part (e.g., a precursor task, a subroutine, or a portion) of operation 620, in which the sensor data analyzer 520 determines the temporal rate of change of the force. In operation 720, the sensor data analyzer 520 calculates a ratio (e.g., a first ratio or a temporal ratio) of the variation in the magnitude of the force during the time period to the duration of the time period. The variation of the force during the time period in general may be positive or negative. However, in certain example embodiments, the calculation of this ratio uses the absolute value of the variation, while in alternative example embodiments, the positive or negative sign of the variation is preserved through the calculation of the ratio. In example embodiments that include operation 720, the generation of the graphical representation 300 in operation 640 is based on the ratio calculated in operation 720.

Operation 730 may be performed as part of operation 630, in which the sensor data analyzer 520 determines the spatial rate of change of the force. In operation 730, the sensor data analyzer 520 calculates a ratio (e.g., a second ratio or a spatial ratio) of the variation in the magnitude of the force during the time period to the incremental distance traveled by the distal portion of the elongate device 110 during the time period. As noted above, the variation of the force during the time period in general may be positive or negative. However, in certain example embodiments, the calculation of this ratio uses the absolute value of the variation, while in alternative example embodiments, the positive or negative sign of the variation is preserved through the calculation of the ratio. In example embodiments that include operation 730, the generation of the graphical representation 300 in operation 640 is based on the ratio calculated in operation 730.

In some example embodiments, one or more weighting coefficients are applied to the current value of the magnitude of the force, the temporal rate of change in the magnitude of the force (e.g., as calculated in operation 620), the spatial rate of change in the magnitude of the force (e.g., as calculated in operation 630), or any suitable combination thereof. In such example embodiments, operations 740 and 744 may be performed at any suitable point prior to operation 640.

In operation 740, the sensor data analyzer 520 determines a set of weighting coefficients to be applied to the current value of the magnitude of the force, the temporal rate of change in the magnitude of the force, and the spatial rate of change in the magnitude of the force.

In certain example embodiments, this set of weighting coefficients is user-specified, and operation 741 may accordingly be performed as part of operation 740. In operation 741, the sensor data analyzer 520 detects a user-submitted command (e.g., submitted by the operator 140) that specifies the set of weighting coefficients to be applied. This detection may be performed by receiving the command or an indication thereof. The specified set of weighting coefficients may correspond to a combination of human health conditions that are specific to the patient 130 (e.g., age, sex, genetics, injury, disease, medical history, diet, exercise, sleep pattern, medication, and the like).

In alternative example embodiments, the set of weighting coefficients is a predetermined set of weighting coefficients, and the predetermined set may be selected from a plurality of multiple predetermined sets of weighting coefficients. For example, the predetermined set may be or include a preset profile that corresponds to a particular situation, such as a particular demographic of the patient 130, a particular health condition to be treated, or a particular preference of the operator 140 for how to operate the elongate device 110. Accordingly, in such alternative example embodiments, operation 742 may be performed as part of operation 740. In operation 742, the sensor data analyzer 520 selects such a predetermined set of weighting coefficients from the plurality of multiple predetermined sets of weighting coefficients. The multiple predetermined sets may each correspond to a different combination of human health conditions, and the selected predetermined set may accordingly correspond to a combination of human health conditions specific to the patient 130.

With the set of weighting coefficients having been determined, in operation 744, the sensor data analyzer 520 mathematically weights the current value of the magnitude of the force, the temporal rate of change in the magnitude of the force, and the spatial rate of change in the magnitude of the force in accordance with their respective weighting coefficients specified in the determined set of weighting coefficients. In example embodiments that include operations 740 and 744, the generating of the graphical representation 300 in operation 640 is based on the weighted current value of the magnitude of the force, the weighted temporal rate of change, and the weighted spatial rate of change.

As shown in FIG. 7, one or both of operations 746 and 748 may be performed as part of operation 640, in which the graphics generator 530 generates the graphical representation 300 of the force. In operation 746, the graphics generator 530 determines a color of at least a portion of the graphical representation 300 (e.g., a group of pixels or a region of the graphical representation 300, such as the alert notification illustrated in FIG. 3), and the color of this portion may be determined based on the temporal rate of change in the magnitude of the force (e.g., as determined in operation 620). Accordingly, in example embodiments that include operation 746, the causing of the display screen 120 to present the graphical representation 300 in operation 650 causes the display screen 120 to present the portion whose color is determined based on the temporal rate of change.

In operation 748, the graphics generator 530 determines a color of at least a portion of the graphical representation 300 (e.g., a group of pixels or a region of the graphical representation 300, such as the alert notification illustrated in FIG. 3), and the color of this portion may be determined based on the spatial rate of change in the magnitude of the force (e.g., as determined in operation 630). Accordingly, in example embodiments that include operation 748, the causing of the display screen 120 to present the graphical representation 300 in operation 650 causes the display screen 120 to present the portion whose color is determined based on the spatial rate of change.

Figure 8:
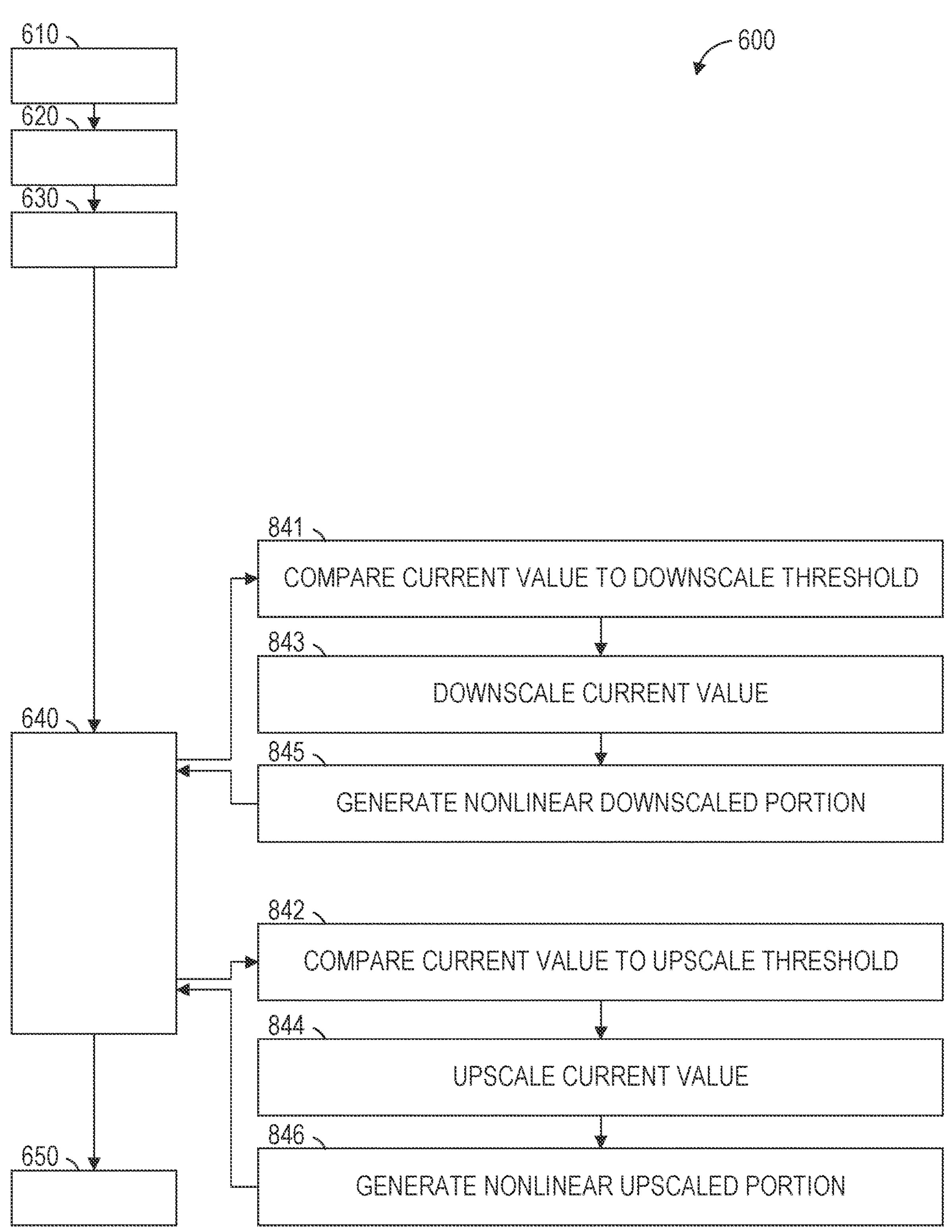

As shown in FIG. 8, in addition to any one or more the operations previously described, the method 600 may include upscaling or downscaling of the current value of the magnitude of the force and graphical depiction thereof by respectively either including operations 841, 843, and 845, or including operations 842, 844, and 846. In either case, the set of included operations may be performed as part of operation 640, in which the graphics generator 530 generates the graphical representation 300 of the force.

In operation 841, the graphics generator 530 compares the current value of the magnitude of the force to a threshold value for the magnitude of the force. The compared threshold value may be a predetermined threshold value (e.g., a predetermined maximum value or a predetermined downscale threshold value).

In operation 843, the graphics generator 530 downscales the current value of the magnitude of the force based on the comparing performed in operation 841. For example, the graphics generator 530 may apply a downscaling coefficient to the current value (e.g., by multiplying the current value by the downscaling coefficient, which may have a value that falls between zero and one) in response to the current value being greater than or equal to the predetermined threshold value compared in operation 841. This may have the effect of introducing nonlinearity to the current magnitude of the magnitude of the force and propagating that nonlinearity into how the current magnitude is represented in the graphical representation 300.

As noted above, according to some example embodiments, a non-linear scaling function is used instead of a comparison to a threshold value. In such example embodiments, operation 841 may be omitted, and operation 843 may instead include calculation of the downscaled value by inputting the current value into the non-linear scaling function (e.g., $f(x)=x^3$) and obtaining the output therefrom.

In operation 845, the graphics generator 530 generates a nonlinear (e.g., scaled down nonlinearly) portion of the graphical representation 300 of the force based on the downscaled current value of the magnitude of the force (e.g., as calculated in operation 843). The resulting graphical representation 300 may accordingly include the generated nonlinear portion, as a result of the current value of the magnitude of the force either transgressing or failing to transgress the predetermined threshold value compared in operation 841.

In operation 842, the graphics generator 530 compares the current value of the magnitude of the force to a threshold value for the magnitude of the force. The compared threshold value may be a predetermined threshold value (e.g., a predetermined minimum value or a predetermined upscale threshold value).

In operation 844, the graphics generator 530 upscales the current value of the magnitude of the force based on the comparing performed in operation 842. For example, the graphics generator 530 may apply an upscaling coefficient to the current value (e.g., by multiplying the current value by the upscaling coefficient, which may have a value greater than one) in response to the current value being less than or equal to the predetermined threshold value compared in operation 842. This may have the effect of introducing nonlinearity to the current magnitude of the magnitude of the force and propagating that nonlinearity into how the current magnitude is represented in the graphical representation 300.

As noted above, according to some example embodiments, a non-linear scaling function is used instead of a comparison to a threshold value. In such example embodiments, operation 842 may be omitted, and operation 844 may instead include calculation of the upscaled value by inputting the current value into the non-linear scaling function (e.g., $f(x)=x^3$) and obtaining the output therefrom.

In operation 846, the graphics generator 530 generates a nonlinear (e.g., scaled up nonlinearly) portion of the graphical representation 300 of the force based on the upscaled current value of the magnitude of the force (e.g., as calculated in operation 844). The resulting graphical representation 300 may accordingly include the generated nonlinear portion, as a result of the current value of the magnitude of the force either transgressing or failing to transgress the predetermined threshold value compared in operation 842.

Figure 9:
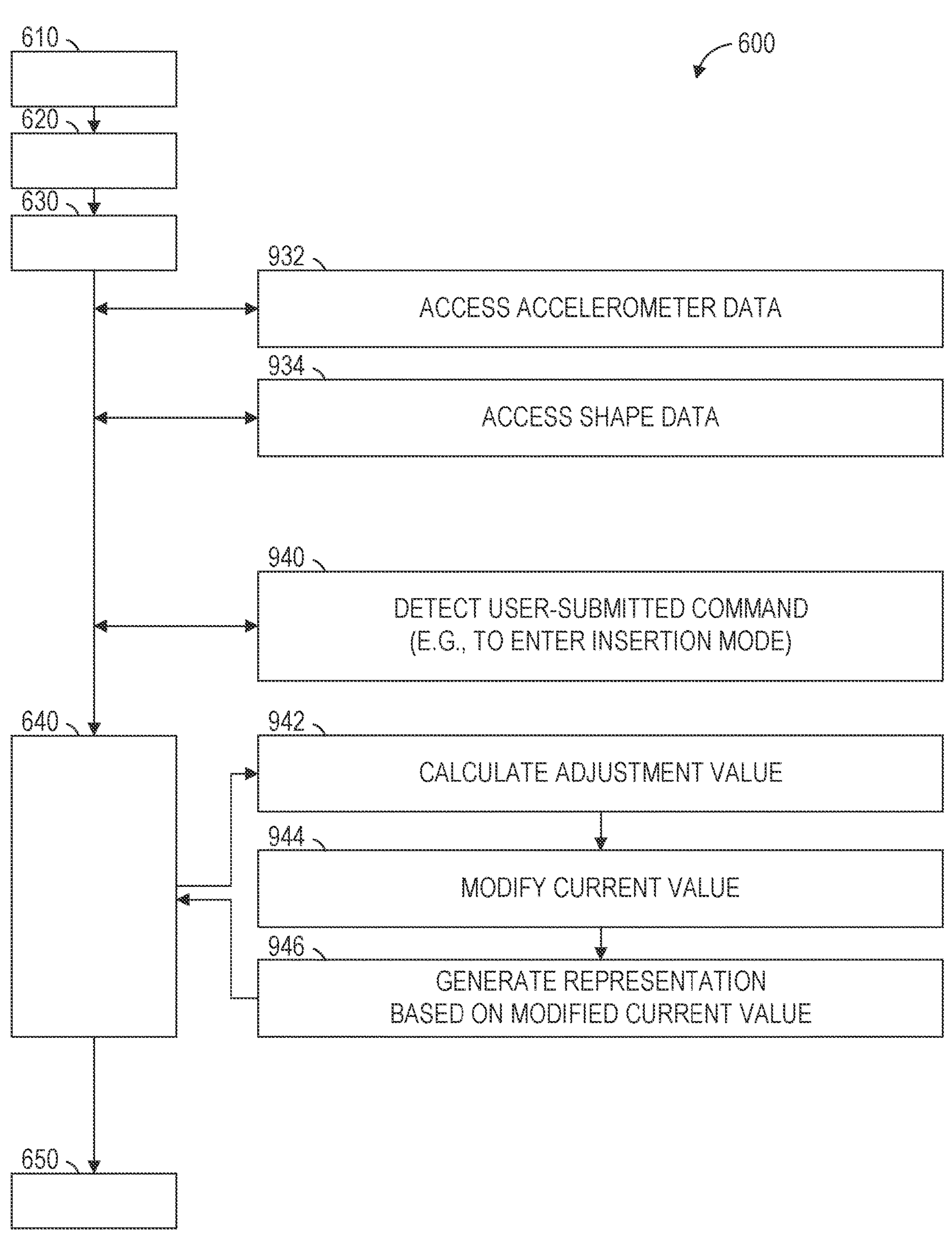

As shown in FIG. 9, in addition to any one or more of the operations previously described, the method 600 may include one or more of operations 932, 934, 940, 942, 944, and 946. One or both of operations 932 and 934 may be performed at any point prior to operation 640, in which the graphics generator 530 generates the graphical representation 300 of the force.

In operation 932, the sensor interface 510 accesses acceleration data generated by the accelerometer 210. As noted above, the accelerometer 210 may be coupled to the elongate device 110 and configured to measure acceleration (e.g., due to gravity, friction, or both) encountered by the elongate device 110 or a portion thereof. In example embodiments that include operation 932, the generation of the graphical representation of the force 300 by the graphics generator 530 in operation 640 is based on the accelerometer data accessed in operation 932.

In operation 934, the sensor interface 510 accesses shape data generated by the shape detector 220. As noted above, the shape detector 220 may be coupled to the elongate device 110 and configured to detect a shape of the elongate device 110 (e.g., detecting positions, orientations, or both of multiple segments of the elongate device 110). In example embodiments that include operation 934, the generation of the graphical representation of the force 300 by the graphics generator 530 in operation 640 is based on the shape data accessed in operation 934.

In operation 940, the sensor interface 510 detects a user-submitted command (e.g., from the operator 140) that the elongate device 110 operate in a mode (e.g., an insertion mode or a device insertion mode) in which frictional and gravitational forces on at least the distal portion of the elongate device 110 are to be disregarded in generating the graphical representation 300 of the force. According to various example embodiments, when the elongate device 110 is operating in such a mode, the frictional and gravitational forces are indicated or otherwise determinable (e.g., calculable) based on the temporal rate of change in the magnitude of the force (e.g., as determined in operation 620), the spatial rate of change in the magnitude of the force (e.g., as determined in operation 630), or both, along with potentially one or more additional factors, such as the accelerometer data accessed in operation 932, the shape data accessed in operation 934, position data (e.g., indicating a position of the distal portion of the elongate device 110), velocity data (e.g., indicating a velocity of the distal portion of the elongate device 110), or any suitable combination thereof.

In example embodiments that include operation 940, operations 942, 944, 946 may be performed as part of operation 640, in which the graphics generator 530 generates the graphical representation 300 of the force. In operation 942, the sensor data analyzer 520 calculates an adjustment value by calculating an estimate of cumulative influences (e.g., cumulative forces) from the frictional and gravitational forces acting upon at least the distal portion of the elongate device 110. The adjustment value may be calculated based on the temporal rate of change in the magnitude of the force (e.g., as determined in operation 620), the spatial rate of change in the magnitude of the force (e.g., as determined in operation 630), or both. According to various example embodiments, one or more additional factors contribute to the calculation of the adjustment value, such as the accelerometer data accessed in operation 932, the shape data accessed in operation 934, or both. In certain example embodiments, the adjustment value is calculated as an estimated proportion (e.g., a percentage) of force attributable to the frictional and gravitational forces, rather than an estimated amount (e.g., a value) of the force.

In operation 944, the sensor data analyzer 520 modifies the current value of the magnitude of the force based on the adjustment value calculated in operation 942. For example, the sensor data analyzer 520 may modify the current value by subtracting the adjustment value from the current value. In example embodiments in which the adjustment value is calculated as an estimated percentage of force, the sensor data analyzer 520 modifies the current value by reducing the current value by the estimated percentage (e.g., by multiplying the current value to an intermediate quantity found by subtracting the estimated percentage from unity).

In operation 946, the graphics generator 530 generates the graphical representation 300 of the force based on the modified current value of the magnitude of the force (e.g., as resultant from performance of operation 944). This may be performed in response to the user-submitted command detected in operation 940. Accordingly, in situations where the operator 140 has commanded the control system 100 to operate the elongate device 110 in a mode that disregards frictional and gravitational forces on at least the distal portion of the elongate device 110, the generated and presented graphical representation 300 of the force is accordingly modified (e.g., by using the adjustment value calculated in operation 942) to visually reflect operation in the commanded mode.

Figure 11:
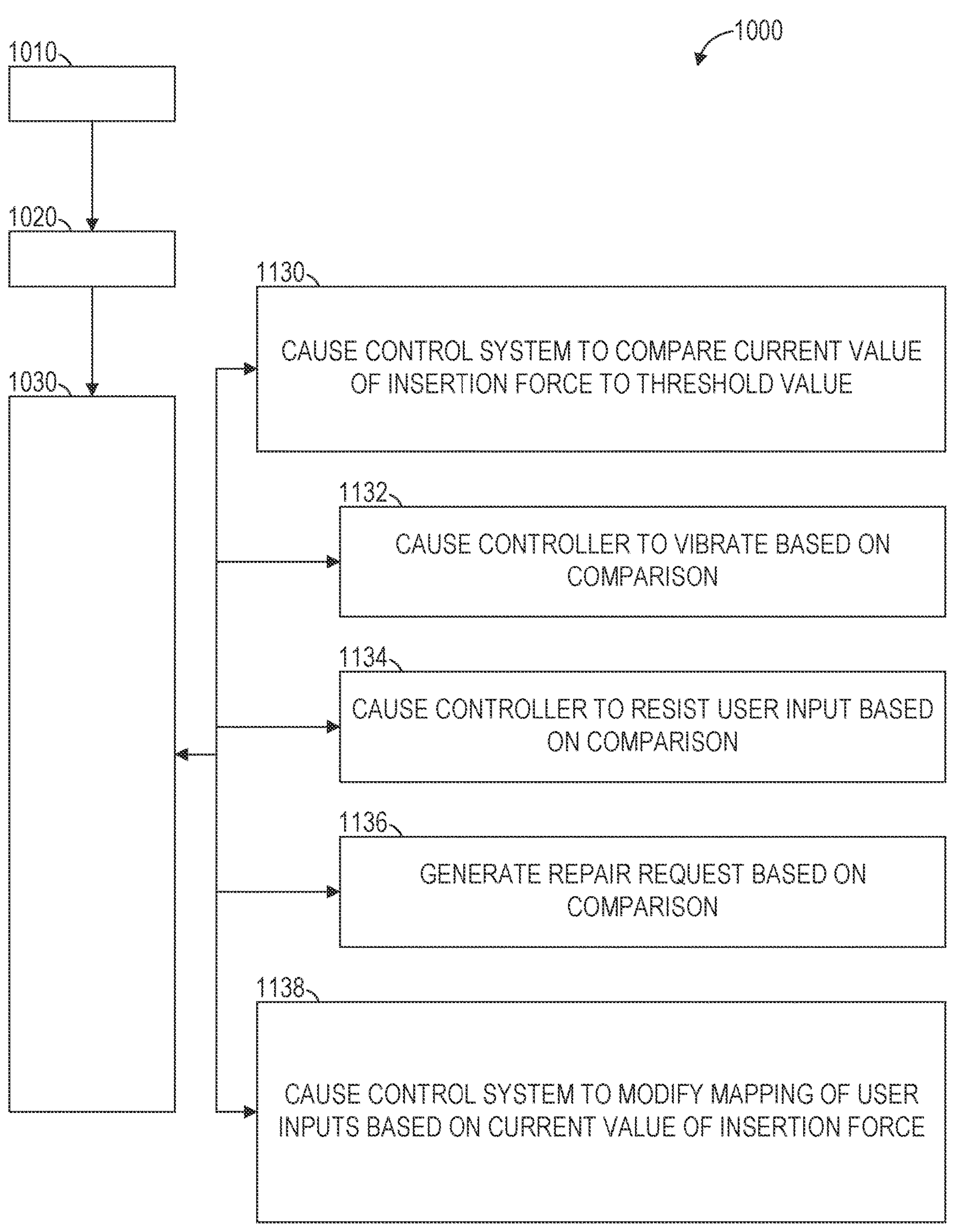
Figure 12:
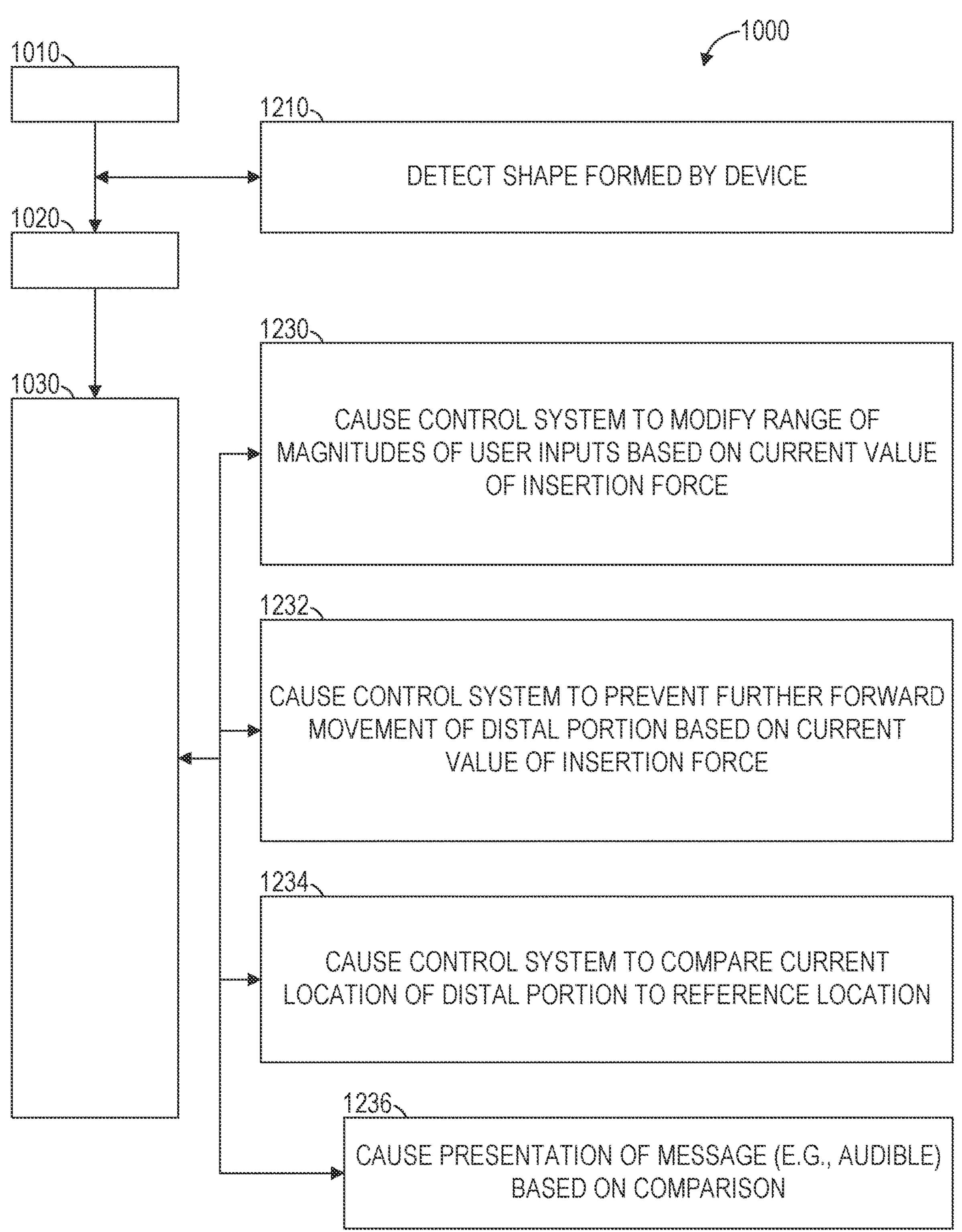

FIGS. 10-12 are flowcharts illustrating operation of the control system 100 (e.g., as described above with respect to FIG. 5, in the context described above with respect to FIGS. 1 and 2, or both) in performing a method 1000 of providing feedback about the elongate device 110, control of the elongate device 110, or both, based on an insertion force (e.g., identified from among multiple forces detected by the force sensor 200), according to some example embodiments. Operations in the method 1000 may be performed using components (e.g., modules) described above with respect to FIG. 5, using one or more processors (e.g., microprocessors or other hardware processors), or using any suitable combination thereof. As shown in FIG. 10, the method 1000 includes operations 1010, 1020, and 1030.

In operation 1010, the sensor interface 510 accesses force data generated by the force sensor 200. As noted above, the force sensor may be communicatively coupled to the proximal portion of the elongate device 110, whose distal portion is configured to travel within an environment, such as within the anatomy of the patient 130. In such example embodiments, the force sensor 200 is configured to detect forces and generate the force data based on the detected forces (e.g., an insertion force, along with one or more other forces, such as a gravitational force, an internal frictional force, or any suitable combination thereof).

In operation 1020, the sensor data analyzer 520 identifies an insertion force based on the force data accessed in operation 1010. In particular, the sensor data analyzer 520 identifies an insertion force encountered by the distal portion of the elongate device 110 (e.g., isolated or otherwise distinguished from among one or more various other forces also detected by the force sensor 200).

In operation 1030, the application 500 initiates a responsive operation performed by the control system 100. The responsive operation may be selected based on the identified insertion force, initiated based on the identified insertion force, or both. In such example embodiments, the control system 100 is communicatively coupled to the elongate device 110 (e.g., for controlling movements of the elongate device 110).

As shown in FIG. 11, in addition to any one or more of the operations previously described for the method 1000, the method 1000 may include one or more of operations 1130, 1132, 1134, 1136, and 1138, which may be performed as part (e.g., a precursor task, a subroutine, or a portion) of operation 1030, in which the application 500 initiates the responsive operation performed by the control system 100.

In operation 1130, as part of initiating the responsive operation, the application 500 causes (e.g., requests, commands, or triggers) the control system 100 to perform a comparison of a current value of the insertion force to a threshold value (e.g., a predetermined maximum or minimum value) for the insertion force. In example embodiments that include operation 1130, one or more resulting responsive operations may be initiated based on (e.g., in response to) this comparing of the current value of the insertion force to the threshold value for the insertion force.

In operation 1132, as part of initiating the responsive operation, the application 500 causes the control system 100 to provide haptic feedback based on the comparison performed in operation 1130. As noted above, the control system 100 may include a control device or other input device (e.g., a partially or fully hand-operated controller), and performance of operation 1132 may thus include causing the control device to vibrate based on the comparison of the current value of the insertion force to the threshold value for the insertion force.

In operation 1134, as part of initiating the responsive operation, the application 500 causes the control system 100 to resist one or more user inputs based on the comparison performed in operation 1130. As noted above, the control system 100 may include a control device or other input device (e.g., a partially or fully hand-operated controller), and performance of operation 1134 may thus include causing the control device to resist attempts by a user, such as the operator 140 (e.g., a surgeon operating the control device during a robotic surgery), to send a user input that would drive the distal portion of the elongate device 110 forward, for example, based on the comparison of the current value of the insertion force to the threshold value for the insertion force (e.g., when the current value exceeds a maximum value for the insertion force).

In operation 1136, as part of initiating the responsive operation, the application 500 causes the control system 100 to generate a repair request (e.g., for repair of the elongate device 110, repair of the control system 100, or both) based on the comparison performed in operation 1130. The generation of the repair request may be accompanied by presentation of one or more alerts (e.g., visible, audible, or both), one or more recommendations (e.g., that the robotic surgical procedure in progress be halted), or any suitable combination thereof. In some example embodiments, the shape formed by the elongate device 110 (e.g., as detected by the shape detector 220) is another factor in causing the control system 100 to generate the repair request. Once generated, the repair request may be sent to the user (e.g., the operator 140), to a servicer or manufacturer of the control system 100, to a servicer or manufacturer of the elongate device 110, or any suitable combination thereof.

In operation 1138, as part of initiating the responsive operation, the application 500 causes the control system 100 to modify (e.g., via scaling or rescaling) a mapping of user inputs to magnitudes of movements by the distal portion of the elongate device 110. This may be performed based on the current value of the insertion force (e.g., alone or in comparison to a threshold value). For example, such a mapping may be stored by the control system 100 (e.g., in a control device or an interface thereto), and the mapping may define or otherwise specify how much movement by the distal portion of the elongate device 110 will result from a certain magnitude of user input at the control device. Based on the current value of the insertion force (e.g., relative to, or in comparison to, one or more threshold values for the insertion force), the control system 100 adjusts the mapping to increase or decrease the sensitivity of the distal portion to a given user input at the control device. As an example, if the current value of the insertion force rises above a maximum value, the sensitivity may be decreased such that a smaller movement (e.g., a smaller forward movement) of the distal portion will result from the same user input (e.g., a forward push on a joystick on the control device). As another example, if the current value of the insertion force drops below a minimum value, the sensitivity may be increased such that a larger movement (e.g., a larger forward movement) for the distal portion will result from the same user input (e.g., a forward push on the joystick).

In some example embodiments, the mapping that is modified in operation 1138 maps magnitudes of user inputs to magnitudes of movement by the distal portion of the elongate device 110. In certain example embodiments, the mapping maps directional information of user inputs to directions of movement by the distal portion of the elongate device 110. In hybrid example embodiments, the mapping maps both magnitudes and directions of user inputs to magnitudes and directions of movements by the distal portion. In further example embodiments, the mapping that is modified maps rates (e.g., velocities) of user inputs to magnitudes of movement by the distal portion of the elongate device 110. In still further example embodiments, the mapping maps magnitudes of user inputs, rates of user inputs, directions of user inputs, or any suitable combination thereof, to corresponding magnitudes, rates, or directions of movements by the distal portion.

As shown in FIG. 12, in addition to any one or more of the operations previously described for the method 1000, the method 1000 may include one or more of operations 1210, 1230, 1232, 1234, and 1236. Operation 1210 may be performed at any point prior to operation 1020, in which the sensor data analyzer 520 identifies the insertion force based on the force data. In operation 1210, the shape detector 220 detects a shape formed by the elongate device 110 and generates corresponding shape data that describes or otherwise represents the detected shape. The shape data is thus usable by the sensor data analyzer 520 in performing operation 1020 to identify the insertion force (e.g., based on both the force data and the shape data). Furthermore, the shape data may be used as an input or other basis for performing operation 1234, which is discussed below.

As shown in FIG. 12, one or more of operations 1230, 1232, 1234, and 1236 may be performed as part (e.g., a precursor task, a subroutine, or a portion) of operation 1030, in which the application 500 initiates the responsive operation performed by the control system 100. In operation 1230, as part of initiating the responsive operation, the application 500 causes the control system 100 to modify a range of magnitudes of user inputs. This may be performed based on the current value of the insertion force (e.g., alone or in comparison to a threshold value). For example, such a range may be stored by the control system 101 (e.g., in a control device or an interface thereto), and the range may define or otherwise specify one or more limits on permissible, recognizable, or otherwise available magnitudes of user inputs for causing (e.g., controlling) movements by the distal portion of the elongate device 110. Based on the current value of the insertion force (e.g., relative to, or in comparison to, one or more threshold values for the insertion force), the control system 100 adjusts the range to expand or shrink the available magnitudes of user input that will cause movement of the distal portion. As an example, if the current value of the insertion force rises above a maximum value, the range may be shrunk such that only relatively small movements (e.g., small in speed, small in distance traveled, or both) of the distal portion will result, regardless how great the user input on the control device. As another example, if the current value of the insertion force drops below a minimum value, the range may be expanded such that relatively larger movements are permitted to be commanded by correspondingly larger user inputs.

In operation 1232, as part of initiating the responsive operation, the application 500 causes the control system 100 to prevent the control device (e.g., a controller operated by the operator 140) from initiating further (e.g., forward) movement of the distal portion of the elongate device 110. This may be performed based on the current value of the insertion force (e.g., alone or in comparison to a threshold value). For example, if the current value of the insertion force rises above a threshold value for the insertion force, the control system 100 may block, ignore, or disable forward movement of the distal portion.

In operation 1234, as part of initiating the responsive operation, the application 500 causes the control system 100 to perform a comparison of a current location of the distal portion of the elongate device 110 to a reference location of the distal portion of the elongate device 110. For example, the current location of the distal portion may be determined (e.g., by the application 500) based on the detecting of the shape formed by the elongate device 110, as discussed above with respect to operation 1210. Thus, the detected shape may indicate the current location of the distal portion of the elongate device 110 within the environment (e.g., within the patient 130). The reference location may correspond to a robotic surgical procedure in progress, and the reference location may be stored by the control system 100 (e.g., in the application 500).

In operation 1236, as part of initiating the responsive operation, the application 500 causes the control system 100 to present (e.g., play) a message (e.g., an audible alert, such as a beep, a tone, or an alert message, whether prerecorded or synthesized, or a displayed message, such as in a pop-up window or other graphical user interface element). The presenting of the message may be performed based on a comparison of a current value of the insertion force to a threshold value, as discussed above with respect to operation 1130. In some example embodiments, the presenting of the message is based on the shape formed by the elongate device 110 (e.g., as detected in operation 1234). In hybrid example embodiments, the current value of the insertion force and the detected shape of the elongate device are both factors in presenting the message.

The presented message may be or include a recommendation, such as a recommendation to alter a workflow in a robotic surgery in progress (e.g., to withdraw the elongate device 110 from the patient 130, to re-lubricate the elongate device 110, to alter a configuration of the elongate device 110, to seek service for the elongate device 110, or any suitable combination thereof). In some example embodiments, the presenting of the message is accompanied by generation of a repair request, as described above with respect to operation 1136.

According to various example embodiments, one or more of the systems and methodologies described herein may facilitate generation of the graphical representation 300 of force encountered by the elongate device 110 or a portion (e.g., the distal portion) thereof. Moreover, one or more of the methodologies described herein may facilitate increased awareness of the elongate device 110 with a portion thereof within the environment (e.g., the anatomy of the patient 130) in which the elongate device 110 is deployed. Such increased awareness may include more accurate and more precise awareness of the location, position, orientation, speed, and heading of the distal portion of the elongate device relative to one or more anatomical structures within the anatomy of the patient 130. Hence, one or more of the methodologies described herein may facilitate intuitive control and management of medical instruments, including elongate devices, such as flexible and steerable catheters, that are suitable for performing minimally invasive medical techniques, as well as improved precision and accuracy of performing such medical techniques and the resulting health benefits for patients, compared to capabilities of pre-existing systems and methods.

Additionally, one or more of the systems and methodologies described herein may facilitate providing haptic (e.g., vibrational) force feedback to a user operating the elongate device 110, scaling how user input is mapped to controlling movements of the distal portion of the elongate device 110, providing an alert regarding the insertion force on the elongate device 110, providing a recommendation to alter a workflow in performing a robotic surgery, resisting one or more user inputs, preventing results of one or more user inputs, or any suitable combination thereof. Accordingly, one or more of the methodologies discussed herein may facilitate increased awareness of the distal portion of the elongate device 110 and its location within the environment in which it is deployed, as well as increased awareness of the potential for further progress in performing the procedure within the environment and the potential for harming the environment, the elongate device 110, or both. Hence, one or more of the methodologies discussed herein may facilitate increased control of the elongate device 110, increased sense of control of the elongate device 110, increased operational effectiveness (e.g., speed, precision, accuracy, efficiency, or any suitable combination thereof), increased patient safety, increased patient comfort, reduced surgery time, reduced surgery costs, reduced recovery time, reduced mechanical wear on the elongate device 110, reduced risk of damage to the elongate device 110, or any suitable combination thereof.

When these effects are considered in aggregate, one or more of the systems and methodologies described herein may obviate a need for certain efforts or resources that otherwise would be involved in generation of a graphical representation of force encountered by elongate device. Efforts expended by a user (e.g., the operator 140) in estimating or otherwise interpreting how much force is being encountered by the elongate device 110 may be reduced by use of (e.g., reliance upon) a special-purpose machine that implements one or more of the methodologies described herein. Computing resources used by one or more systems or machines may similarly be reduced (e.g., compared to systems or machines that lack the structures discussed herein or are otherwise unable to perform the functions discussed herein). Examples of such computing resources include processor cycles, network traffic, computational capacity, main memory usage, graphics rendering capacity, graphics memory usage, data storage capacity, power consumption, and cooling capacity.

Figure 13:
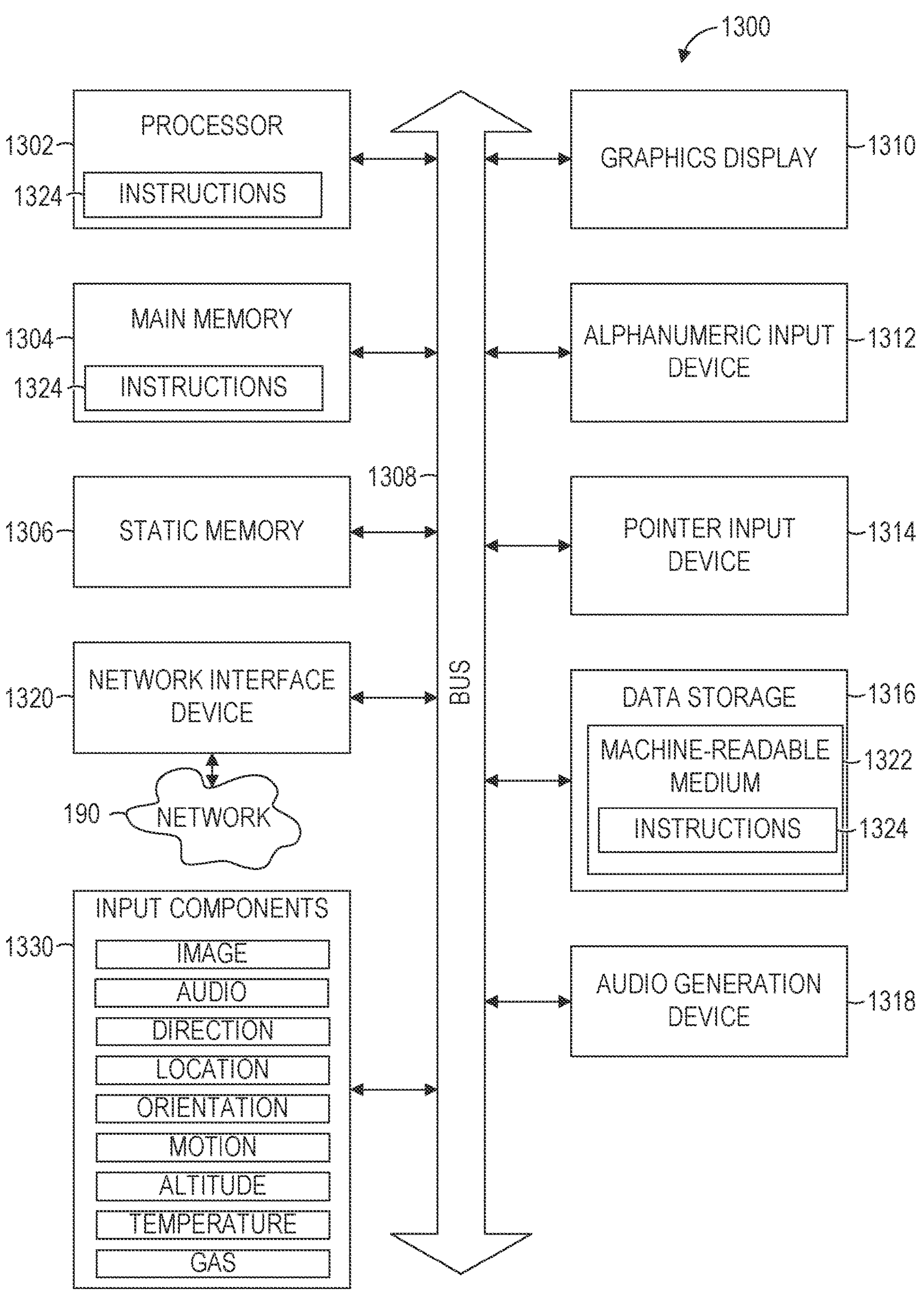
FIG. 13 is a block diagram illustrating components of a machine, according to some example embodiments, able to read instructions from a machine-readable medium and perform any one or more of the methodologies discussed herein.

FIG. 13 is a block diagram illustrating components of a machine 1300, according to some example embodiments, able to read instructions 1324 from a machine-readable medium 1322 (e.g., a non-transitory machine-readable medium, a machine-readable storage medium, a computer-readable storage medium, or any suitable combination thereof) and perform any one or more of the methodologies discussed herein, in whole or in part. Specifically, FIG. 13 shows the machine 1300 in the example form of a computer system (e.g., a computer) within which the instructions 1324 (e.g., software, a program, an application, an applet, an app, or other executable code) for causing the machine 1300 to perform any one or more of the methodologies discussed herein may be executed, in whole or in part.

In alternative embodiments, the machine 1300 operates as a standalone device or may be communicatively coupled (e.g., networked) to other machines. In a networked deployment, the machine 1300 may operate in the capacity of a server machine or a client machine in a server-client network environment, or as a peer machine in a distributed (e.g., peer-to-peer) network environment. The machine 1300 may be a server computer, a client computer, a personal computer (PC), a tablet computer, a laptop computer, a netbook, a cellular telephone, a smart phone, a set-top box (STB), a personal digital assistant (PDA), a web appliance, a network router, a network switch, a network bridge, or any machine capable of executing the instructions 1324, sequentially or otherwise, that specify actions to be taken by that machine. Further, while only a single machine is illustrated, the term "machine" shall also be taken to include any collection of machines that individually or jointly execute the instructions 1324 to perform all or part of any one or more of the methodologies discussed herein.

The machine 1300 includes a processor 1302 (e.g., one or more central processing units (CPUs), one or more graphics processing units (GPUs), one or more digital signal processors (DSPs), one or more application specific integrated circuits (ASICs), one or more radio-frequency integrated circuits (RFICs), or any suitable combination thereof), a main memory 1304, and a static memory 1306, which are configured to communicate with each other via a bus 1308. The processor 1302 contains solid-state digital microcircuits (e.g., electronic, optical, or both) that are configurable, temporarily or permanently, by some or all of the instructions 1324 such that the processor 1302 is configurable to perform any one or more of the methodologies described herein, in whole or in part. For example, a set of one or more microcircuits of the processor 1302 may be configurable to execute one or more modules (e.g., software modules) described herein. In some example embodiments, the processor 1302 is a multicore CPU (e.g., a dual-core CPU, a quad-core CPU, an 8-core CPU, or a 128-core CPU) within which each of multiple cores behaves as a separate processor that is able to perform any one or more of the methodologies discussed herein, in whole or in part. Although the beneficial effects described herein may be provided by the machine 1300 with at least the processor 1302, these same beneficial effects may be provided by a different kind of machine that contains no processors (e.g., a purely mechanical system, a purely hydraulic system, or a hybrid mechanical-hydraulic system), if such a processor-less machine is configured to perform one or more of the methodologies described herein.

The machine 1300 may further include a graphics display 1310 (e.g., a plasma display panel (PDP), a light emitting diode (LED) display, a liquid crystal display (LCD), a projector, a cathode ray tube (CRT), or any other display capable of displaying graphics or video). The machine 1300 may also include an alphanumeric input device 1312 (e.g., a keyboard or keypad), a pointer input device 1314 (e.g., a mouse, a touchpad, a touchscreen, a trackball, a joystick, a stylus, a motion sensor, an eye tracking device, a data glove, or other pointing instrument), a data storage 1316, an audio generation device 1318 (e.g., a sound card, an amplifier, a speaker, a headphone jack, or any suitable combination thereof), and a network interface device 1320.

The data storage 1316 (e.g., a data storage device) includes the machine-readable medium 1322 (e.g., a tangible and non-transitory machine-readable storage medium) on which are stored the instructions 1324 embodying any one or more of the methodologies or functions described herein. The instructions 1324 may also reside, completely or at least partially, within the main memory 1304, within the static memory 1306, within the processor 1302 (e.g., within the processor's cache memory), or any suitable combination thereof, before or during execution thereof by the machine 1300. Accordingly, the main memory 1304, the static memory 1306, and the processor 1302 may be considered machine-readable media (e.g., tangible and non-transitory machine-readable media). The instructions 1324 may be transmitted or received over the network 190 via the network interface device 1320. For example, the network interface device 1320 may communicate the instructions 1324 using any one or more transfer protocols (e.g., hypertext transfer protocol (HTTP)).

In some example embodiments, the machine 1300 may be a portable computing device (e.g., a smart phone, a tablet computer, or a wearable device), and may have one or more additional input components 1330 (e.g., sensors or gauges). Examples of such input components 1330 include an image input component (e.g., one or more cameras), an audio input component (e.g., one or more microphones), a direction input component (e.g., a compass), a location input component (e.g., a global positioning system (GPS) receiver), an orientation component (e.g., a gyroscope), a motion detection component (e.g., one or more accelerometers), an altitude detection component (e.g., an altimeter), a temperature input component (e.g., a thermometer), and a gas detection component (e.g., a gas sensor). Input data gathered by any one or more of these input components 1330 may be accessible and available for use by any of the modules described herein (e.g., with suitable privacy notifications and protections, such as opt-in consent or opt-out consent, implemented in accordance with user preference, applicable regulations, or any suitable combination thereof).

As used herein, the term "memory" refers to a machine-readable medium able to store data temporarily or permanently and may be taken to include, but not be limited to, random-access memory (RAM), read-only memory (ROM), buffer memory, flash memory, and cache memory. While the machine-readable medium 1322 is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of carrying (e.g., storing or communicating) the instructions 1324 for execution by the machine 1300, such that the instructions 1324, when executed by one or more processors of the machine 1300 (e.g., processor 1302), cause the machine 1300 to perform any one or more of the methodologies described herein, in whole or in part. Accordingly, a "machine-readable medium" refers to a single storage apparatus or device, as well as cloud-based storage systems or storage networks that include multiple storage apparatus or devices. The term "machine-readable medium" shall accordingly be taken to include, but not be limited to, one or more tangible and non-transitory data repositories (e.g., data volumes) in the example form of a solid-state memory chip, an optical disc, a magnetic disc, or any suitable combination thereof.

A "non-transitory" machine-readable medium, as used herein, specifically excludes propagating signals per se. According to various example embodiments, the instructions 1324 for execution by the machine 1300 can be communicated via a carrier medium (e.g., a machine-readable carrier medium). Examples of such a carrier medium include a non-transient carrier medium (e.g., a non-transitory machine-readable storage medium, such as a solid-state memory that is physically movable from one place to another place) and a transient carrier medium (e.g., a carrier wave or other propagating signal that communicates the instructions 1324).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module in which the hardware includes one or more processors. Accordingly, the operations described herein may be at least partially processor-implemented, hardware-implemented, or both, since a processor is an example of hardware, and at least some operations within any one or more of the methods discussed herein may be performed by one or more processor-implemented modules, hardware-implemented modules, or any suitable combination thereof.

Moreover, such one or more processors may perform operations in a "cloud computing" environment or as a service (e.g., within a "software as a service" (SaaS) implementation). For example, at least some operations within any one or more of the methods discussed herein may be performed by a group of computers (e.g., as examples of machines that include processors), with these operations being accessible via a network (e.g., the Internet) and via one or more appropriate interfaces (e.g., an application program interface (API)). The performance of certain operations may be distributed among the one or more processors, whether residing only within a single machine or deployed across a number of machines. In some example embodiments, the one or more processors or hardware modules (e.g., processor-implemented modules) may be located in a single geographic location (e.g., within a home environment, an office environment, or a server farm). In other example embodiments, the one or more processors or hardware modules may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and their functionality presented as separate components and functions in example configurations may be implemented as a combined structure or component with combined functions. Similarly, structures and functionality presented as a single component may be implemented as separate components and functions. These and other variations, modifications, additions, and improvements fall within the scope of the subject matter herein.

Some portions of the subject matter discussed herein may be presented in terms of algorithms or symbolic representations of operations on data stored as bits or binary digital signals within a memory (e.g., a computer memory or other machine memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "accessing," "processing," "detecting," "computing," "calculating," "determining," "generating," "presenting," "displaying," or the like refer to actions or processes performable by a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

The following enumerated descriptions describe various examples of methods, machine-readable media, and systems (e.g., machines, devices, or other apparatus) discussed herein.

A first example provides a system comprising:

an elongate device (e.g., a flexible elongate device) including a distal portion configured to travel within an environment (e.g., and including a proximal portion configured to remain external to the environment);

a force sensor coupled to the elongate device (e.g., coupled to the proximal portion thereof) and configured to detect (e.g., measure) a force (e.g., a force encountered by the distal portion of the elongate device during a time period in which the distal portion travels a distance within the environment), the force sensor being configured to generate force data based on the detected (e.g., measured) force;

a display screen;

one or more processors; and a memory storing instructions that, when executed by at least one processor among the one or more processors, cause the at least one processor to perform operations comprising:

accessing the force data generated by the force sensor, the force data quantifying variation in magnitude of the force encountered by the distal portion of the elongate device during the time period in which the distal portion traveled the distance within the environment, the force data including a current value of the magnitude of the force;

determining a temporal rate of change of the force during the time period based on the force data and the time period;

determining a spatial rate of change of the force based on the force data and the distance traveled by the distal portion of the elongate device;

generating a graphical representation (e.g., a real-time graphical representation) of the force based on the current value of the magnitude of the force, the temporal rate of change of the force, and the spatial rate of change of the force; and causing the display screen to present the graphical representation generated based on the current value, the temporal rate of change, and the spatial rate of change.

A second example provides a system according to the first example, wherein:

the determining of the temporal rate of change of the force includes calculating a ratio of the variation in the magnitude of the force to a duration of the time period in which the distal portion of the elongate device traveled the distance within the environment; and the generating of the graphical representation of the force is based on the ratio of the variation in the magnitude of the force to the duration of the time period.

A third example provides a system according to the first example or the second example, wherein:

the determining of the spatial rate of change of the force includes calculating a ratio of the variation in the magnitude of the force to the distance traveled by the distal portion of the elongate device within the environment; and the generating of the graphical representation of the force is based on the ratio of the variation in the magnitude of the force to the distance traveled by the distal portion.

A fourth example provides a system according to any of the first through third examples, wherein:

the generating of the graphical representation of the force includes determining a color of at least a portion of the graphical representation based on the temporal rate of change of the force; and the causing of the display screen to present the graphical representation includes causing the display screen to present the portion whose color is determined based on the temporal rate of change of the force.

A fifth example provides a system according to any of the first through fourth examples, wherein:

the generating of the graphical representation of the force includes determining a color of at least a portion of the graphical representation based on the spatial rate of change of the force; and the causing of the display screen to present the graphical representation includes causing the display screen to present the portion whose color is determined based on the spatial rate of change of the force.

A sixth example provides a system according to any of the first through fifth examples, wherein the operations further comprise:

weighting the current value of the magnitude of the force, the temporal rate of change of the force, and the spatial rate of change of the force; and wherein:

the generating of the graphical representation of the force is based on the weighted current value, the weighted temporal rate of change, and the weighted spatial rate of change.

A seventh example provides a system according to the sixth example, wherein the operations further comprise:

determining a set of weighting coefficients for the current value of the magnitude of the force, the temporal rate of change of the force, and the spatial rate of change of the force; and wherein:

the weighting of the current value of the force, the temporal rate of change of the force, and the spatial rate of change of the force is based on the determined set of weighting coefficients.

An eighth example provides a system according to the seventh example, wherein:

the determining of the set of weighting coefficients includes detecting a user-submitted command that specifies the set of weighting coefficients; and the weighting of the current value of the force, the temporal rate of change of the force, and the spatial rate of change of the force is based on the set of weighting coefficients specified by the user-submitted command.

A ninth example provides a system according to the seventh example, wherein:

the determining of the set of weighting coefficients includes selecting a predetermined set of weighting coefficients from a plurality of predetermined sets of weighting coefficients; and the weighting of the current value of the force, the temporal rate of change of the force, and the spatial rate of change of the force is based on the predetermined set selected from the plurality of predetermined sets.

A tenth example provides a system according to the ninth example, wherein:

each predetermined set of weighting coefficients in the plurality of predetermined sets of weighting coefficients corresponds to a different combination of human health conditions.

An eleventh example provides a system according to any of the first through tenth examples, wherein:

the generating of the graphical representation of the force includes: comparing the current value of the magnitude of the force to a threshold value; downscaling the current value of the magnitude of the force based on the comparing; and generating a nonlinear portion of the graphical representation of the force, the nonlinear portion depicting the downscaled current value of the magnitude of the force.

A twelfth example provides a system according to any of the first through tenth examples, wherein:

the generating of the graphical representation of the force includes: comparing the current value of the magnitude of the force to a threshold value;

upscaling the current value of the magnitude of the force based on the comparing; and generating a nonlinear portion of the graphical representation of the force, the nonlinear portion depicting the upscaled current value of the magnitude of the force.

A thirteenth example provides a system according to any of the first through twelfth examples, further comprising:

an accelerometer coupled to the elongate device and configured to detect (e.g., measure) an acceleration encountered by the elongate device during the time period in which the distal portion travels the distance within the environment, the accelerometer being configured to generate acceleration data based on the detected (e.g., measured) acceleration; wherein the operations further comprise:

accessing the acceleration data generated by the accelerometer; and wherein the generating of the graphical representation of the force is based on the accelerometer data.

A fourteenth example provides a system according to any of the first through thirteenth examples, further comprising:

a shape detector coupled to the elongate device and configured to detect a shape of the elongate device during the time period in which the distal portion travels the distance within the environment, the shape detector being configured to generate shape data based on the detected shape; wherein the operations further comprise:

accessing the shape data generated by the shape detector; and wherein the generating of the graphical representation of the force is based on the shape data.

A fifteenth example provides a system according to any of the first through fourteenth examples, wherein the operations further comprise:

detecting a user-submitted command that the elongate device operate in a device insertion mode in which frictional and gravitational forces on the distal portion of the elongate device are to be disregarded; and wherein:

the generating of the graphical representation of the force includes:

calculating an adjustment value that estimates influences from frictional and gravitational forces on the distal portion of the elongate device, the adjustment value being calculated based on the temporal and spatial rates of change of the force;

modifying the current value of the magnitude of the force by subtracting the calculated adjustment value therefrom; and generating the graphical representation of the force based on the modified current value of the magnitude of the force in response to the user-submitted command that the elongate device operate in the insertion mode.

A sixteenth example provides a system according to any of the first through fifteenth examples, wherein:

the environment in which the distal portion of the elongate device travels the distance is an anatomy of a human patient;

the elongate device is a flexible robotic surgical catheter that has an axial direction from a proximal portion of the flexible robotic surgical catheter to the distal portion of the flexible robotic surgical catheter;

the force encountered by the distal portion of the flexible robotic surgical catheter is detected (e.g., measured) by an axial force sensor during the time period in which the distal portion travels the distance within the anatomy of the human patient; and the force data is generated by the axial force sensor and quantifies variation in the magnitude of the axial force applied to the distal portion of the flexible robotic surgical catheter against its axial direction.

A seventeenth example provides a method comprising:

accessing, by one or more processors, force data generated by a force sensor, the force data quantifying variation in magnitude of a force encountered by a distal portion of an elongate device during a time period in which the distal portion traveled a distance within an environment, the force data including a current value of the magnitude of the force;

determining, by one or more of the processors, a temporal rate of change of the force during the time period based on the force data and the time period;

determining, by one or more of the processors, a spatial rate of change of the force based on the force data and the distance traveled by the distal portion of the elongate device;

generating, by one or more of the processors, a graphical representation (e.g., a real-time graphical representation) of the force based on the current value of the magnitude of the force, the temporal rate of change of the force, and the spatial rate of change of the force; and causing, by one or more of the processors, a display screen to present the graphical representation generated based on the current value, the temporal rate of change, and the spatial rate of change.

An eighteenth example provides a method according to the seventeenth example, wherein:

the generating of the graphical representation of the force includes determining a color of at least a portion of the graphical representation based on the spatial rate of change of the force; and the causing of the display screen to present the graphical representation includes causing the display screen to present the portion whose color is determined based on the spatial rate of change of the force.

A nineteenth example provides a machine-readable medium (e.g., a non-transitory machine-readable storage medium) comprising instructions that, when executed by one or more processors of a machine, cause the machine to perform operations comprising:

accessing force data generated by a force sensor, the force data quantifying variation in magnitude of a force encountered by a distal portion of an elongate device during a time period in which the distal portion traveled a distance within an environment, the force data including a current value of the magnitude of the force;

determining a temporal rate of change of the force during the time period based on the force data and the time period;

determining a spatial rate of change of the force based on the force data and the distance traveled by the distal portion of the elongate device;

generating a graphical representation (e.g., a real-time graphical representation) of the force based on the current value of the magnitude of the force, the temporal rate of change of the force, and the spatial rate of change of the force; and causing a display screen to present the graphical representation generated based on the current value, the temporal rate of change, and the spatial rate of change.

A twentieth example provides a machine-readable medium according to the nineteenth example, wherein:

the determining of the spatial rate of change of the force includes calculating a ratio of the variation in the magnitude of the force to the distance traveled by the distal portion of the elongate device within the environment; and the generating of the graphical representation of the force is based on the ratio of the variation in the magnitude of the force to the distance traveled by the distal portion.

A twenty-first example provides a machine-readable medium according to the nineteenth example, wherein:

the generating of the graphical representation resource includes:

generating a graphical bar among a sequence of graphical bars, the sequence having an axis, the generated graphical bar having a cross-axis length that represents the current value of the magnitude of the force and an axis-aligned length that represents the time period in which the distal portion traveled the distance within the environment.

A twenty-second example provides a system comprising:

a flexible elongate device including a distal portion configured to travel within an environment and a proximal portion configured to remain external to the environment;

a force sensor coupled to the proximal portion of the flexible elongate device and configured to detect forces and generate force data based on the detected forces; and a control system communicatively coupled to the flexible elongate device and the force sensor, the control system being configured to:

based on the force data, identify an insertion force encountered by the distal portion of the flexible elongate device from among the forces detected by the force sensor; and based on the identified insertion force encountered by the distal portion, initiate a responsive operation performed by the control system.

A twenty-third example provides a system according to the twenty-second example, further comprising:

a controller configured to detect user inputs and initiate corresponding movements of the distal portion of the flexible elongate device within the environment; and wherein:

the responsive operation performed by the control system includes performing a comparison of a current value of the identified insertion force to a threshold value and causing the controller to vibrate based on the comparison.

A twenty-fourth example provides a system according to the twenty-second example or the twenty-third example, further comprising:

if not already present, a controller configured to detect user inputs and initiate corresponding movements of the distal portion of the flexible elongate device within the environment; and wherein:

the responsive operation performed by the control system includes performing a comparison of a current value of the identified insertion force to a threshold value and causing the controller to resist a user input based on the comparison.

A twenty-fifth example provides a system according to any of the twenty-second through twenty-fourth examples, further comprising:

if not already present, a controller configured to detect user inputs and initiate corresponding movements of the distal portion of the flexible elongate device within the environment; and wherein:

the responsive operation performed by the control system includes, based on a current value of the insertion force, modifying a mapping of magnitudes of user inputs from the controller to magnitudes of movements by the distal portion of the flexible elongate device.

A twenty-sixth example provides a system according to any of the twenty-second through twenty-fifth examples, further comprising:

if not already present, a controller configured to detect user inputs and initiate corresponding movements of the distal portion of the flexible elongate device within the environment; and wherein:

the responsive operation performed by the control system includes, based on a current value of the insertion force, modifying a mapping of directional user inputs from the controller to directions of movements by the distal portion of the flexible elongate device.

A twenty-seventh example provides a system according to any of the twenty-second through twenty-sixth examples, further comprising:

if not already present, a controller configured to detect user inputs and initiate corresponding movements of the distal portion of the flexible elongate device within the environment; and wherein:

the responsive operation performed by the control system includes, based on a current value of the insertion force, modifying a range of magnitudes of user inputs from the controller.

A twenty-eighth example provides a system according to any of the twenty-second through twenty-seventh examples, further comprising:

if not already present, a controller configured to detect user inputs and initiate corresponding movements of the distal portion of the flexible elongate device within the environment; and wherein:

the responsive operation performed by the control system includes, based on a current value of the insertion force, preventing the controller from initiating further forward movement of the distal portion of the flexible elongate device.

A twenty-ninth example provides a system according to any of the twenty-second through twenty-eighth examples, wherein:

the responsive operation performed by the control system includes performing a comparison of a current value of the identified insertion force to a threshold value and causing presentation of an audible message based on the comparison.

A thirtieth example provides a system according to any of the twenty-second through twenty-ninth examples, wherein:

the responsive operation performed by the control system includes performing a comparison of a current value of the identified insertion force to a threshold value of the insertion force and the generating a repair request based on the comparison.

A thirty-first example provides a system according to any of the twenty-second through thirtieth examples, further comprising:

a shape detector configured to detect a shape formed by the flexible elongate device, the detected shape indicating a current location of the distal portion of the flexible elongate device within the environment, and wherein:

the responsive operation performed by the control system includes performing a comparison of the current location of the distal portion of the flexible elongate device to a reference location of the distal portion of the flexible elongate device and causing presentation of an audible message based on the comparison.

A thirty-second example provides a method comprising:

accessing, by one or more processors, force data generated by a force sensor communicatively coupled to a proximal portion of a flexible elongate device that has a distal portion configured to travel within an environment, the force sensor being configured to detect forces and generate the force data therefrom;

based on the force data, and by one or more of the processors, identifying an insertion force encountered by the distal portion of the flexible elongate device from among the forces detected by the force sensor; and based on the identified insertion force, and by one or more of the processors, initiating a responsive operation performed by a control system communicatively coupled to the flexible elongate device.

A thirty-third example provides a method according to the thirty-second example, wherein:

the control system is communicatively coupled to a controller configured to detect user inputs and initiate corresponding movements of the distal portion of the flexible elongate device within the environment, and the initiating of the responsive operation performed by the control system includes causing the control system to perform a comparison of a current value of the identified insertion force to a threshold value and causing the controller to vibrate based on the comparison.

A thirty-fourth example provides a method according to the thirty-second example or the thirty-third example, wherein:

the control system is communicatively coupled to a controller configured to detect user inputs and initiate corresponding movements of the distal portion of the flexible elongate device within the environment; and the initiating of the responsive operation performed by the control system includes causing the control system to perform a comparison of a current value of the identified insertion force to a threshold value and causing the controller to resist a user input based on the comparison.

A thirty-fifth example provides a method according to any of the thirty-second through thirty-fourth examples, wherein:

the control system is communicatively coupled to a controller configured to detect user inputs and initiate corresponding movements of the distal portion of the flexible elongate device within the environment; and the initiating of the responsive operation performed by the control system includes, based on a current value of the insertion force, causing the control system to modify a mapping of magnitudes of user inputs from the controller to magnitudes of movements by the distal portion of the flexible elongate device.

A thirty-sixth example provides a method according to any of the thirty-second through thirty-fifth examples, wherein:

the control system is communicatively coupled to a controller configured to detect user inputs and initiate corresponding movements of the distal portion of the flexible elongate device within the environment; and the initiating of the responsive operation performed by the control system includes, based on a current value of the insertion force, causing the control system to modify a mapping of directional user inputs from the controller to directions of movements by the distal portion of the flexible elongate device.

A thirty-seventh example provides a method according to any of the thirty-second through thirty-sixth examples, wherein:

the control system is communicatively coupled to a controller configured to detect user inputs and initiate corresponding movements of the distal portion of the flexible elongate device within the environment; and the initiating of the responsive operation performed by the control system includes, based on a current value of the insertion force, causing the control system to modify a range of magnitudes of user inputs from the controller.

A thirty-eighth example provides a method according to any of the thirty-second through thirty-seventh examples, wherein:

the control system is communicatively coupled to a controller configured to detect user inputs and initiate corresponding movements of the distal portion of the flexible elongate device within the environment; and the initiating of the responsive operation performed by the control system includes, based on a current value of the insertion force, causing the control system to prevent the controller from initiating further forward movement of the distal portion of the flexible elongate device.

A thirty-ninth example provides a method according to any of the thirty-second through thirty-eighth examples, wherein:

the initiating of the responsive operation performed by the control system includes causing the control system to perform a comparison of a current value of the identified insertion force to a threshold value of the insertion force and then generating a repair request based on the comparison.

A fortieth example provides a method according to any of the thirty-second through thirty-ninth examples, wherein:

the control system is communicatively coupled to a shape detector configured to detect a shape formed by the flexible elongate device, the detected shape indicating a current location of the distal portion of the flexible elongate device within the environment; and the initiating of the responsive operation performed by the control system includes causing the control system to perform a comparison of the current location of the distal portion of the flexible elongate device to a reference location of the distal portion of the flexible elongate device and causing presentation of an audible message based on the comparison.

A forty-first example provides a machine-readable medium, (e.g., a non-transitory machine-readable storage medium) comprising instructions that, when executed by one or more processors of a machine, cause the machine to perform operations comprising:

accessing force data generated by a force sensor communicatively coupled to a proximal portion of a flexible elongate device that has a distal portion configured to travel within an environment, the force sensor being configured to detect forces and generate the force data therefrom;

based on the force data, identifying an insertion force encountered by the distal portion of the flexible elongate device from among the forces detected by the force sensor; and based on the identified insertion force, initiating a responsive operation performed by a control system communicatively coupled to the flexible elongate device.

A forty-second example provides a carrier medium carrying machine-readable instructions for controlling a machine to carry out the operations (e.g., method operations) performed in any one of the previously described examples.

What is claimed is:

1. A system comprising:

a flexible elongate device including a distal portion configured to travel within an environment and a proximal portion configured to remain external to the environment;

a force sensor coupled to the proximal portion of the flexible elongate device and configured to detect forces and generate force data based on the detected forces; and a control system communicatively coupled to the flexible elongate device and the force sensor, the control system being configured to perform operations comprising:

based on the force data, identifying an insertion force encountered by the distal portion of the flexible elongate device from among the forces detected by the force sensor, the identifying of the insertion force including modifying a current value of the insertion force based on a spatial rate of change in magnitude of the insertion force across a distance traveled by the distal portion within the environment or a temporal rate of change in the magnitude of the insertion force over a time period during which the distal portion traveled the distance within the environment; and based on the identified insertion force encountered by the distal portion, initiating one or more responsive operations performed by the control system, the one or more responsive operations including performing a comparison of a current value of the identified insertion force to a threshold value of the insertion force and then causing a controller of the flexible elongate device to provide haptic feedback based on the current value exceeding the threshold value, the controller being configured to provide the haptic feedback caused by the control system.

2. The system of claim 1, further comprising:

the controller, further configured to detect user inputs and initiate corresponding movements of the distal portion of the flexible elongate device within the environment; and wherein:

the one or more responsive operations performed by the control system include causing the controller to provide the haptic feedback by vibrating in response to the current value exceeding the threshold value.

3. The system of claim 1, further comprising:

the controller, further configured to detect user inputs and initiate corresponding movements of the distal portion of the flexible elongate device within the environment; and wherein:

the one or more responsive operations performed by the control system include causing the controller to provide the haptic feedback by resisting a user input in response to the current value exceeding the threshold value.

4. The system of claim 1, further comprising:

the controller, further configured to detect user inputs and initiate corresponding movements of the distal portion of the flexible elongate device within the environment; and wherein:

the one or more responsive operations performed by the control system include modifying a mapping of magnitudes of user inputs from the controller to magnitudes of movements by the distal portion of the flexible elongate device.

5. The system of claim 1, further comprising:

the controller, further configured to detect user inputs and initiate corresponding movements of the distal portion of the flexible elongate device within the environment; and wherein:

the one or more responsive operations performed by the control system include modifying a mapping of directional user inputs from the controller to directions of movements by the distal portion of the flexible elongate device.

6. The system of claim 1, wherein:

the controller, further configured to detect user inputs and initiate corresponding movements of the distal portion of the flexible elongate device within the environment; and wherein:

the one or more responsive operations performed by the control system include modifying a range of magnitudes of user inputs from the controller.

7. The system of claim 1, further comprising:

the controller, further configured to detect user inputs and initiate corresponding movements of the distal portion of the flexible elongate device within the environment; and wherein:

the one or more responsive operations performed by the control system include preventing the controller from initiating further forward movement of the distal portion of the flexible elongate device.

8. The system of claim 1, wherein:

the one or more responsive operations performed by the control system include causing presentation of an audible message based on the comparison.

9. The system of claim 1, wherein the operations further comprise:

generating a repair request based on a shape formed by the flexible elongate device.

10. The system of claim 1, further comprising:

a shape detector configured to detect a shape formed by the flexible elongate device, the detected shape indicating a current location of the distal portion of the flexible elongate device within the environment; and wherein:

the one or more responsive operations performed by the control system include performing a further comparison of the current location of the distal portion of the flexible elongate device to a reference location of the distal portion of the flexible elongate device and causing presentation of an audible message based on the further comparison.

11. A non-transitory machine-readable storage medium comprising instructions that, when executed by one or more processors of a machine, cause the machine to perform operations comprising:

accessing force data generated by a force sensor communicatively coupled to a proximal portion of a flexible elongate device that has a distal portion configured to travel within an environment, the force sensor being configured to detect forces and generate the force data therefrom;

based on the force data, identifying an insertion force encountered by the distal portion of the flexible elongate device from among the forces detected by the force sensor, the identifying of the insertion force including modifying a current value of the insertion force based on a spatial rate of change in magnitude of the insertion force across a distance traveled by the distal portion within the environment or a temporal rate of change in the magnitude of the insertion force over a time period during which the distal portion traveled the distance within the environment; and based on the identified insertion force, initiating one or more responsive operations performed by a control system communicatively coupled to the flexible elongate device, the one or more responsive operations including performing a comparison of a current value of the identified insertion force to a threshold value of the insertion force and then causing a controller of the flexible elongate device to provide haptic feedback based on the current value exceeding the threshold value, the controller being configured to provide the haptic feedback caused by the control system.

12. The non-transitory machine-readable storage medium of claim 11, wherein:

the control system is communicatively coupled to the controller further configured to detect user inputs and initiate corresponding movements of the distal portion of the flexible elongate device within the environment; and the one or more responsive operations performed by the control system include causing the controller to provide the haptic feedback by vibrating in response to the current value exceeding the threshold value.

13. The non-transitory machine-readable storage medium of claim 11, wherein:

the control system is communicatively coupled to the controller further configured to detect user inputs and initiate corresponding movements of the distal portion of the flexible elongate device within the environment; and the one or more responsive operations performed by the control system include causing the controller to provide the haptic feedback by resisting a user input in response to the current value exceeding the threshold value.

14. The non-transitory machine-readable storage medium of claim 11, wherein:

the control system is communicatively coupled to the controller further configured to detect user inputs and initiate corresponding movements of the distal portion of the flexible elongate device within the environment; and the one or more responsive operations performed by the control system include modifying a mapping of magnitudes of user inputs from the controller to magnitudes of movements by the distal portion of the flexible elongate device.

15. The non-transitory machine-readable storage medium of claim 11, wherein:

the control system is communicatively coupled to the controller further configured to detect user inputs and initiate corresponding movements of the distal portion of the flexible elongate device within the environment; and the one or more responsive operations performed by the control system include modifying a mapping of directional user inputs from the controller to directions of movements by the distal portion of the flexible elongate device.

16. The non-transitory machine-readable storage medium of claim 11, wherein:

the control system is communicatively coupled to the controller further configured to detect user inputs and initiate corresponding movements of the distal portion of the flexible elongate device within the environment; and the one or more responsive operations performed by the control system include modifying a range of magnitudes of user inputs from the controller.

17. The non-transitory machine-readable storage medium of claim 11, wherein:

the control system is communicatively coupled to the controller further configured to detect user inputs and initiate corresponding movements of the distal portion of the flexible elongate device within the environment; and the one or more responsive operations performed by the control system include preventing the controller from initiating further forward movement of the distal portion of the flexible elongate device.

18. The non-transitory machine-readable storage medium of claim 11, wherein the operations further comprise:

generating a repair request based on a shape formed by the flexible elongate device.

19. The non-transitory machine-readable storage medium of claim 11, wherein:

the control system is communicatively coupled to a shape detector configured to detect a shape formed by the flexible elongate device, the detected shape indicating a current location of the distal portion of the flexible elongate device within the environment; and the one or more responsive operations performed by the control system include performing a further comparison of the current location of the distal portion of the flexible elongate device to a reference location of the distal portion of the flexible elongate device and causing presentation of an audible message based on the further comparison.

20. A method comprising:

accessing, by one or more processors, force data generated by a force sensor communicatively coupled to a proximal portion of a flexible elongate device that has a distal portion configured to travel within an environment, the force sensor being configured to detect forces and generate the force data therefrom;

based on the force data, and by one or more of the processors, identifying an insertion force encountered by the distal portion of the flexible elongate device from among the forces detected by the force sensor, the identifying of the insertion force including modifying a current value of the insertion force based on a spatial rate of change in magnitude of the insertion force across a distance traveled by the distal portion within the environment or a temporal rate of change in the magnitude of the insertion force over a time period during which the distal portion traveled the distance within the environment; and based on the identified insertion force, and by one or more of the processors, initiating one or more responsive operations performed by a control system communicatively coupled to the flexible elongate device, the one or more responsive operations including performing a comparison of a current value of the identified insertion force to a threshold value of the insertion force and then causing a controller of the flexible elongate device to provide haptic feedback based on the current value exceeding the threshold value, the controller being configured to provide the haptic feedback caused by the control system.

* * * * *